(12) United States Patent
Hwang et al.

(10) Patent No.: US 11,413,501 B2
(45) Date of Patent: Aug. 16, 2022

(54) METHOD AND SYSTEM OF PLANNING FITNESS COURSES

(71) Applicant: J-MEX, Hsinchu (TW)

(72) Inventors: Deng-Huei Hwang, Hsinchu (TW); Bing-Ho Tsai, Hsinchu (TW); Meng-Yu Lee, Hsinchu (TW)

(73) Assignee: J-Mex Inc., Hsinchu (TW)

( * ) Notice: Subject to any disclaimer, the term of this patent is extended or adjusted under 35 U.S.C. 154(b) by 796 days.

(21) Appl. No.: 16/234,240

(22) Filed: Dec. 27, 2018

(65) Prior Publication Data

US 2019/0192913 A1 Jun. 27, 2019

(30) Foreign Application Priority Data

Dec. 27, 2017 (TW) .................. 106146084

(51) Int. Cl.
*A63B 24/00* (2006.01)
*G09B 5/02* (2006.01)
*G09B 19/00* (2006.01)

(52) U.S. Cl.
CPC ...... *A63B 24/0075* (2013.01); *A63B 24/0006* (2013.01); *A63B 24/0062* (2013.01); *G09B 5/02* (2013.01); *G09B 19/0038* (2013.01); *A63B 2024/0015* (2013.01); *A63B 2024/0065* (2013.01); *A63B 2024/0068* (2013.01); *A63B 2024/0078* (2013.01); *A63B 2220/803* (2013.01); *A63B 2230/06* (2013.01); *A63B 2230/50* (2013.01)

(58) Field of Classification Search
CPC ............ A63B 24/0075; A63B 24/0006; A63B 24/0062; A63B 2024/0015; A63B 2024/0065; A63B 2024/0068; A63B 2024/0078; A63B 2220/803; A63B 2230/06; A63B 2230/50; G09B 5/02; G09B 19/0038
USPC ........................................................ 434/257
See application file for complete search history.

(56) References Cited

U.S. PATENT DOCUMENTS

| 7,905,818 B1 | 3/2011 | Habig |
| 2003/0144829 A1 | 7/2003 | Geatz et al. |
| 2019/0192912 A1* | 6/2019 | Hwang .................. A61B 5/681 |

FOREIGN PATENT DOCUMENTS

| TW | 201716116 A | 5/2017 |
| WO | 2014153201 A1 | 9/2014 |

OTHER PUBLICATIONS

The Office Action for Taiwanese application No. TW201716116 dated Jan. 7, 2019.

* cited by examiner

*Primary Examiner* — Robert P Bullington
(74) *Attorney, Agent, or Firm* — Haverstock & Owens, A Law Corporation

(57) ABSTRACT

A system for planning a fitness exercise course includes a corresponding module establishing a corresponding relationship between a training target and each of a plurality of fitness exercise items, wherein the training target includes a specific muscle, a muscle group and a whole body muscle; a sensing module sensing a physiological state of a body builder; and a determining module, according to the corresponding relationship, in response to the physiological state, selecting one of the plurality of fitness exercise items and a combination of fitness exercise items to complete the training target.

7 Claims, 14 Drawing Sheets

METHOD AND SYSTEM OF PLANNING FITNESS COURSES

CROSS REFERENCE TO RELATED APPLICATION

This application claims the benefit of Taiwan's Patent Application No. 106146084, filed on Dec. 27, 2017, at Taiwan's Intellectual Property Office, the disclosures of which are incorporated herein in their entirety by reference.

TECHNICAL FIELD

Embodiments in the present disclosure are related to a method and a system of planning fitness courses, and more particularly to a method and a system of planning fitness courses using an application of an electronic device.

BACKGROUND

Modern people pay more attention to health, and their concepts and awareness of health are gradually improved. Therefore, a balanced diet and appropriate exercise can not only maintain a healthy body, but also enhance the body's resistance and stay away from the pain and disease. There are many ways to achieve the fitness effect. It is convenient to use the popular mobile device to engage in fitness exercise. With the guidance of the application of the mobile device, the muscles of the desired sculpture can be trained anytime and anywhere. No matter whether you ask the fitness instructor to guide how to use the fitness equipment to train the muscles in the fitness center, or the busy office workers use the spare time of work to freely train the muscle parts of the intended exercise, it is extremely convenient to use the relevant fitness application to guide the operation. In the case of freehand exercise, such as push-ups or sit-ups, the push-ups can mainly exercise the muscles of the upper arms, while the sit-ups can mainly exercise the abdominal muscles and the muscles in the vicinity, and this way for the sedentary office people are more convenient.

However, in addition to mobile devices, in practice, most of these applications run on a single device. Although the stand-alone operation can record an individual's fitness history as a recommendation for a future fitness course, it is still not based on the individual's physical condition to personalize fitness classes.

SUMMARY OF EXEMPLARY EMBODIMENTS

Therefore, it is expected that these fitness applications can be run not only on the electronic device, but also connected to the back-end database or server, etc. If the electronic device is connected to the database in the server, statistics can be done for different fitness people to generate big data, remote servers or mobile devices/PCs can also generate fitness classes based on the big data stored in remote databases, in order to advise a body builder to follow the tailor-made fitness courses for individuals. The app also generates a course of exercise for the exercise equipment to advise the body builder to exercise properly.

In addition, the sensing module can be arranged to the fitness person to sense the physiological parameters of the fitness person. For example, according to the fitness person's heart rate, recovery rate or tiredness level, and whether the intensity of the exercise meets the standard, a fitness exercise course suggestion is provided. It includes suggestions for training different muscle groups or muscles, and the number of repetitions and the total time of exercise completion, and the rest time.

The invention provides a planning method and system for a smart fitness course. The method or system provides the body builder with a proposal for at least one set of trainable muscle groups. Under a predetermined objective to achieve an intended fitness effect, the fitness person can choose a training course including a plurality of set of training item or a plurality of training items according to a physiological state of the fitness person, then refer to the fitness level or fitness experience and skills of the fitness person, adjust the planned training course according to his/her favorite sports, other willingness and his/her experienced fitness course, optimize the various parameters of the fitness courses, make it more suitable for the fitness effect of the bodybuilder in the physical exercise environment and the physical and psychological needs of the bodybuilder.

The present invention provides a system for planning a fitness course by allowing a fitness person to enter the platform via a network by establishing a platform architecture in a cyber space, and operating the system with an application APP. The body builders including trained fitness students, general fitness athletes, and fitness exercise coaches can not only obtain the fitness course content recommended by the system through this platform, but also allow fitness students to receive guidance from fitness coaches through this platform, or consult the fitness instructor, or let the fitness instructor guide the students to carry out effective fitness training. As for the general fitness athletes who do not need coaching, they can also refer to the fitness program recommended by the system for exercise and fitness, and evaluate the fitness results.

The system's consultative suggestion features and platform-based architecture are not only suitable for fitness activities such as gymnasiums with coaches, but also for fitness exercises based on the recommendations of this system.

The present disclosure provides a method for planning a fitness exercise course, comprising the following steps: providing a body builder with tips for at least one set of trainable muscle groups; sensing a plurality of limb motions of the body builder to correspondingly generate a plurality of limb motion sensing signals by using a multiple sensing module; deriving a specific training effect of the set of trainable muscle groups based on the plurality of limb motion sensing signals to determine a training effect datum, wherein the specific training effect is to be achieved by implementing one of a plurality of sets of training items and a plurality of training items; generating a training course datum according to a physiological state of the body builder, wherein the training course datum is configured to comprise one of a first part of training items of the plurality of sets of training items and a first part of training items of the plurality of training items; providing an item-adjustment suggestion for the training course according to at least one of a fitness level datum, a willingness datum and a fitness experience datum of the body builder; and providing a parameter configuration or suggestion on the training course based on the training effect datum to generate a fitness curriculum.

The present disclosure provides a system for planning a fitness exercise course, comprising: a fitness course database storing at least one of a fitness course datum and a fitness exercise datum; a personal fitness course database storing a personal fitness course datum and a personal fitness exercise datum of a body builder; a muscle-group versus fitnessexercise-item logic unit establishing a corresponding data relationship of a muscle training in which a muscle group corresponds to a fitness exercise item; a fitness-effect versus fitness-exercise-item logic unit providing at least one of a plurality of exercise groups and a plurality of exercise items which allow the muscle group to achieve a training effect; a trainable-muscle-group-determining logic unit suggesting at least one of a set of trainable muscle groups and a group of trainable muscles according to a physiological state of the body builder; a-course-item-combination logic unit generating an exercise course configured to represent at least one of a first part of the plurality of exercise groups and a first part of the plurality of exercise items according to the physiological state by the muscle-group versus fitness-exercise-item logic unit; a course-item-adding-or-deleting logic unit providing an item-planning suggestion of the fitness exercise course according to at least one of a fitness level datum, a willingness datum and a fitness experience datum of the body builder; a multiple sensing module correspondingly generating a plurality of limb motion sensing signals by sensing a plurality of limb motions of the body builder to calculate the training effect; a course-parameter-adjustment logic unit providing a parameter-configuration suggestion to the fitness exercise course according to the training effect, wherein the parameter configuration suggestion includes a first plurality of exercise times, a plurality of exercise groups of the fitness exercise course, a second plurality of exercise times in each of the exercise groups, a training time of each of the exercise groups, a rest time between two consecutive exercise groups, a total training time and a total rest time configuration of the fitness exercise course; and a course-content-display logic unit presenting a course content of the fitness exercise course.

The present disclosure provides a system for planning a fitness exercise course, comprising: a corresponding module establishing a corresponding relationship between a training target and each of a plurality of fitness exercise items, wherein the training target includes a specific muscle, a muscle group and a whole body muscle; a sensing module sensing a physiological state of a body builder; and a determining module, according to the corresponding relationship, in response to the physiological state, selecting one of the plurality of fitness exercise items and a combination of fitness exercise items to complete the training target.

The above embodiments and advantages of the present invention will become more readily apparent to those ordinarily skilled in the art after reviewing the following detailed descriptions and accompanying drawings.

DETAILED DESCRIPTION OF THE PREFERRED EMBODIMENTS

Please refer to all Figures of the present invention when reading the following detailed description, wherein all Figs. of the present invention demonstrate different embodiments of the present invention by showing examples, and help the skilled person in the art to understand how to implement the present invention. However, the practical arrangements and the present method provided to implement the present invention is not necessary to completely comply with the descriptions in the specification. The present examples provide sufficient embodiments to demonstrate the spirit of the present invention, each embodiment does not conflict with the others, and new embodiments can be implemented through an arbitrary combination thereof, i.e., the present invention is not restricted to the embodiments disclosed in the present specification.

Figure 1A:
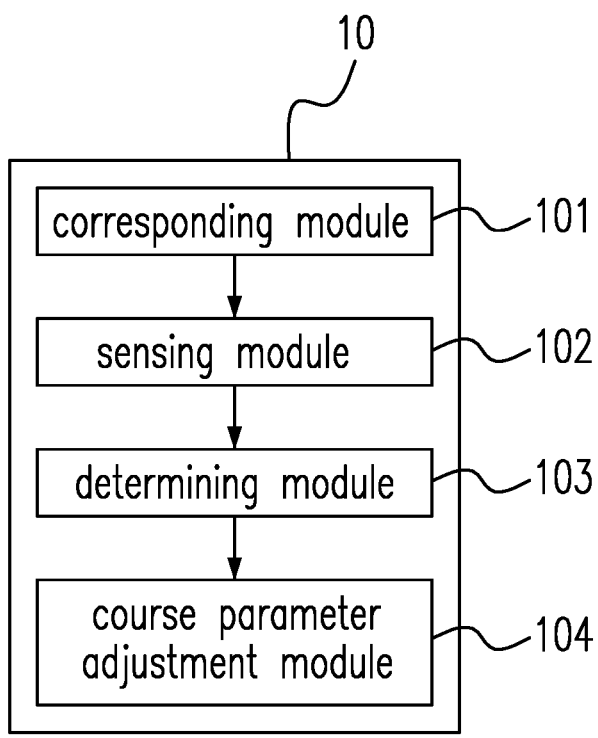
FIG. 1A is a system for planning a fitness course according to a preferred embodiment of the present disclosure.

Please refer to FIG. 1A, which shows a system 10 for planning a fitness course in accordance with a preferred embodiment of the present invention. Please refer to FIG. 1B, which shows a schematic diagram of planning a fitness course for a body builder (or a fitness person) according to a preferred embodiment of the present invention. The system 10 includes a corresponding module 101, a sensing module 102, and a determining module 103. The corresponding module 101 establishes an exercise target including a specific muscle, a muscle group and a whole body muscle, a plurality of fitness exercise items, and a correspondence relationship between the exercise target and each of the plurality of fitness exercises. The sensing module 102 senses (or measures) a physiological state of the fitness person, and the determining module 103 selects one of the plurality of fitness sports items or a combination of the plurality of items according to the corresponding relationship to complete a training of the exercise target.

In FIG. 1A, the corresponding module 101 further establishes the exercise target containing a cardiopulmonary activity. The system 10 is preferably an electronic device such as a smart device, a mobile device, a personal computer PC, or a server. The system 10 further includes a course parameter adjustment module 104 and a processing unit (not shown) configured to implement the corresponding module 101, the determining module 103, and the course parameter adjustment module 104, and generate a fitness course suitable for the fitness person according to the physiological parameters sensed by the sensing module 102. The system 10 stores the fitness course in a database (not shown). The database includes a system fitness course database and a personal fitness course database. If the system 10 includes a remote connection server, the system fitness course database can be configured in the server, the server can generate statistics for different fitness people to generate big data, remote server or mobile device/PC can also generate fitness courses according to the big data stored in the remote database. It is recommended that the fitness person follow the tailor-made fitness course for the individual to exercise.

Figure 1B:
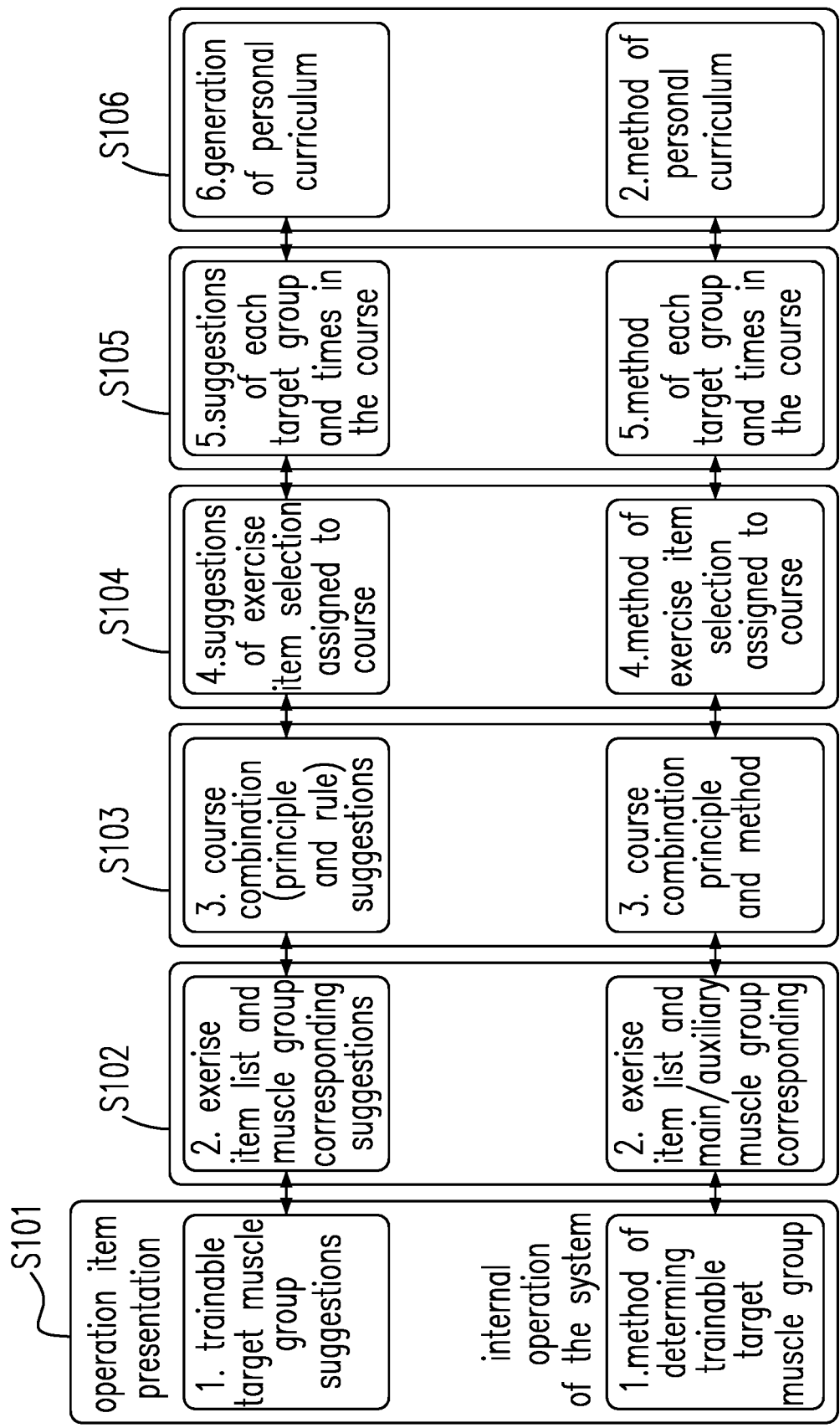
FIG. 1B is a schematic diagram of planning a fitness course for a body builder (or a fitness person) according to a preferred embodiment of the present invention.
Figure 2A:
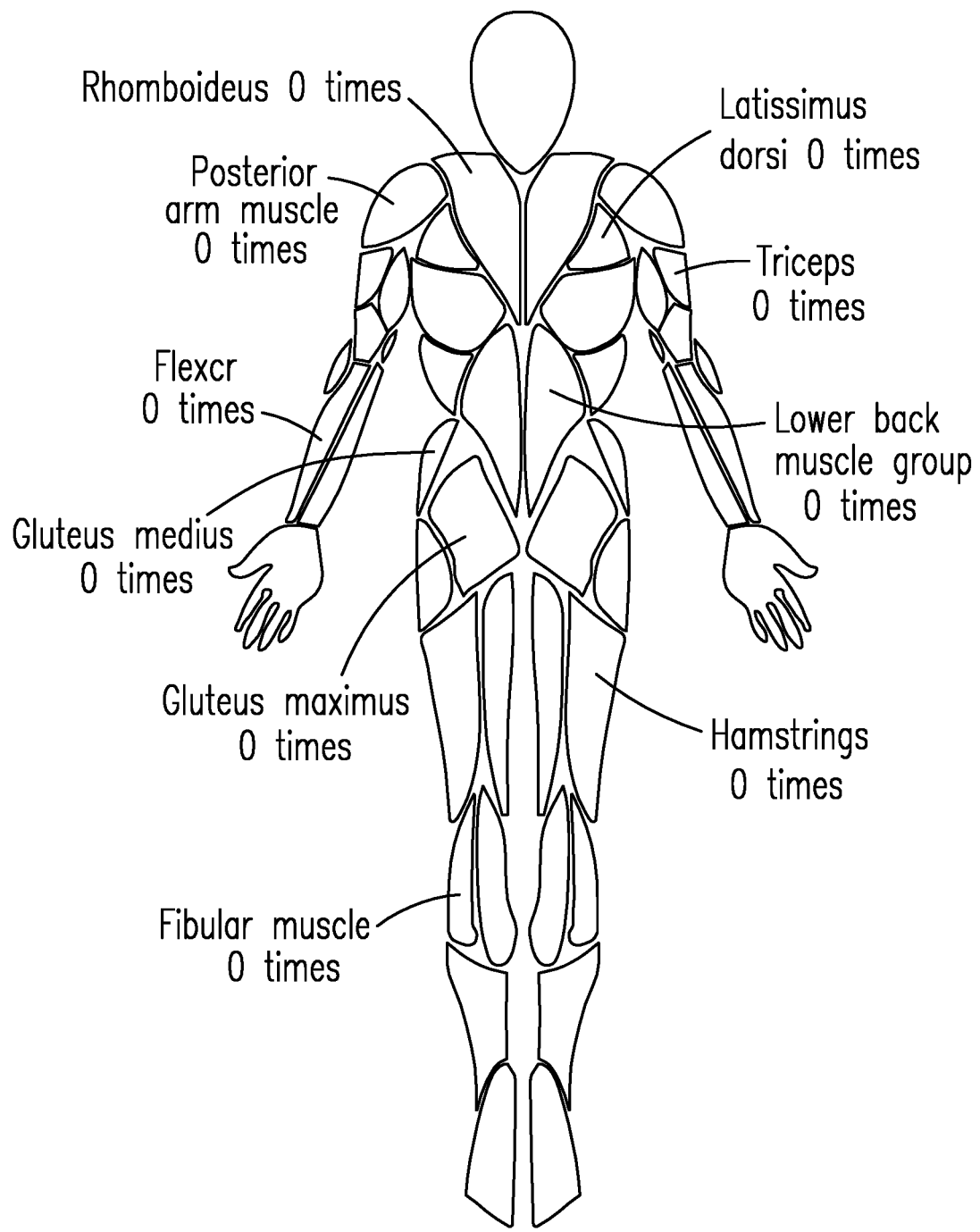
FIG. 2A is a schematic diagram of a predetermined muscle grouping principle according to a preferred embodiment of the present invention.
Figure 2B:
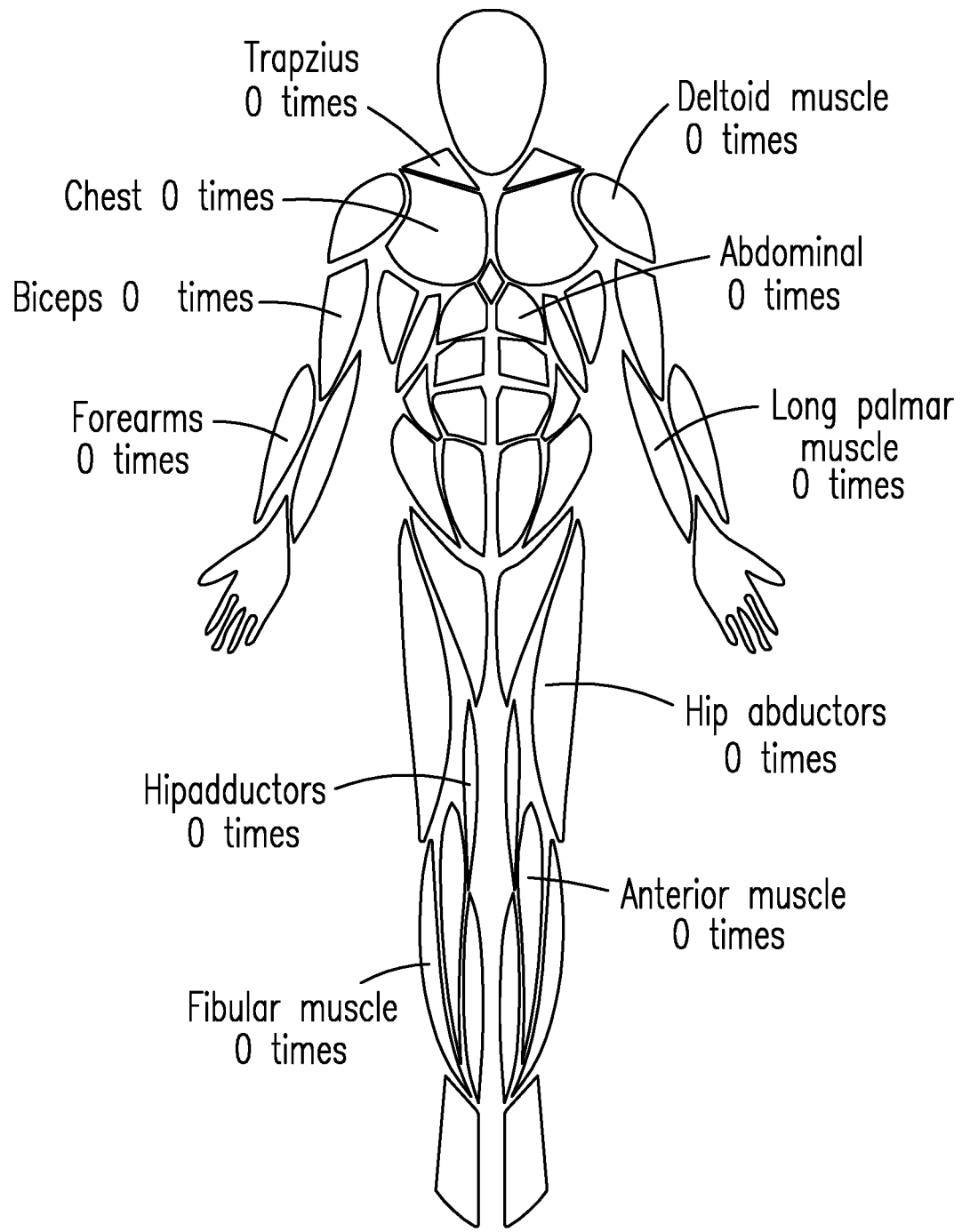
FIG. 2B is a schematic diagram of a predetermined muscle grouping principle according to a preferred embodiment of the present invention.

In FIG. 1B, a schematic diagram of a fitness program for a fitness person includes an operational item presentation and internal operation of the system 10. In step S101, the system 10 suggests a trainable target muscle group, and the system 10 is based on a predetermined muscle grouping principle, as shown in FIGS. 2A and 2B. FIGS. 2A and 2B shows a schematic diagram of a predetermined muscle grouping principle according to a preferred embodiment of the present invention, each of which contains a different muscle group, further illustrated in Table 1 below.

TABLE 1

| Group classification | | Main Muscle Group | | Accessory Muscle Group |
|---|---|---|---|---|
| 1 | Shoulder | 1 | Shoulder | |
| 2 | Upper extremity | 2 | Biceps | |
| | | 3 | Triceps | |
| | | | | 11 Forearms |
| 3 | Upper Body | 4 | Chest | |
| | | 5 | Back | |
| | | | | 12 Trapezius |
| 4 | Lower extremity | 6 | Quadriceps | |
| | | 7 | Hamstrings | |
| | | | | 13 Calves |
| 5 | Glutes | 8 | Glutes | |
| | | | | 14 Hip abductors |
| | | | | 15 Hip adductors |
| 6 | Abs | 9 | Abdominal | |
| | | 10 | Lower Back | |

Table 1 is mainly used to define the smart menu function description and interface presented by the application. The first column in Table 1 is the muscle group classification, the second column is the main muscle group, and the third column is the accessory muscle group. The Main Muscle Group is divided into six subgroups: Shoulder, Upper extremity, Upper Body, Abs, Glutes, and Lower extremity. The Main Muscle Group has the following 10 types: Abdominal, Quadriceps, Chest, Shoulders, Back, Triceps. Biceps, Lower Back, Glutes and Hamstrings. The Accessory Muscle Group includes the trapezius muscle, hip abductors, hip adductors, forearms, and calves.

Figure 3A:
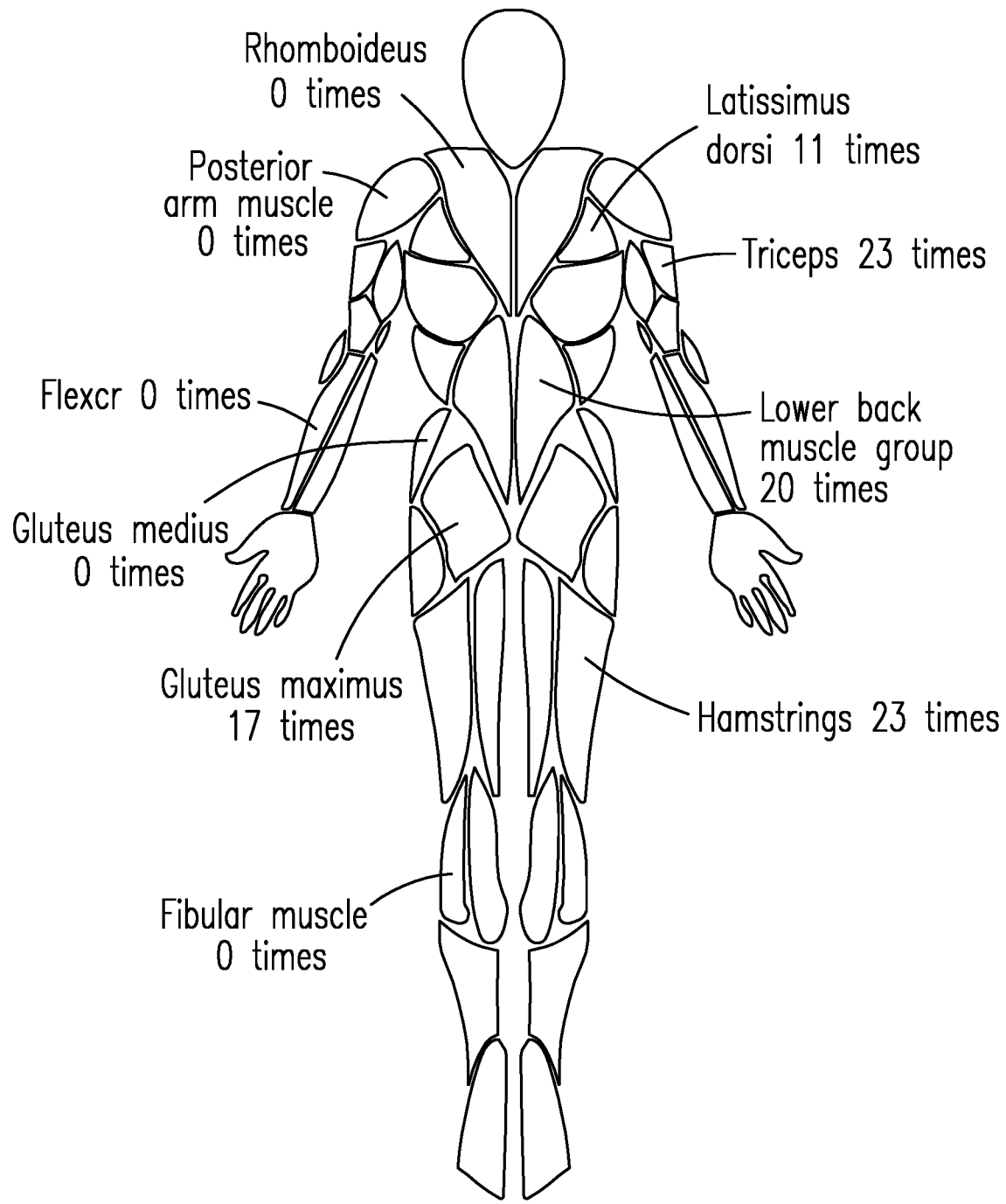
FIG. 3A is a schematic illustration of muscle recovery rates in accordance with a preferred embodiment of the present invention.
Figure 3B:
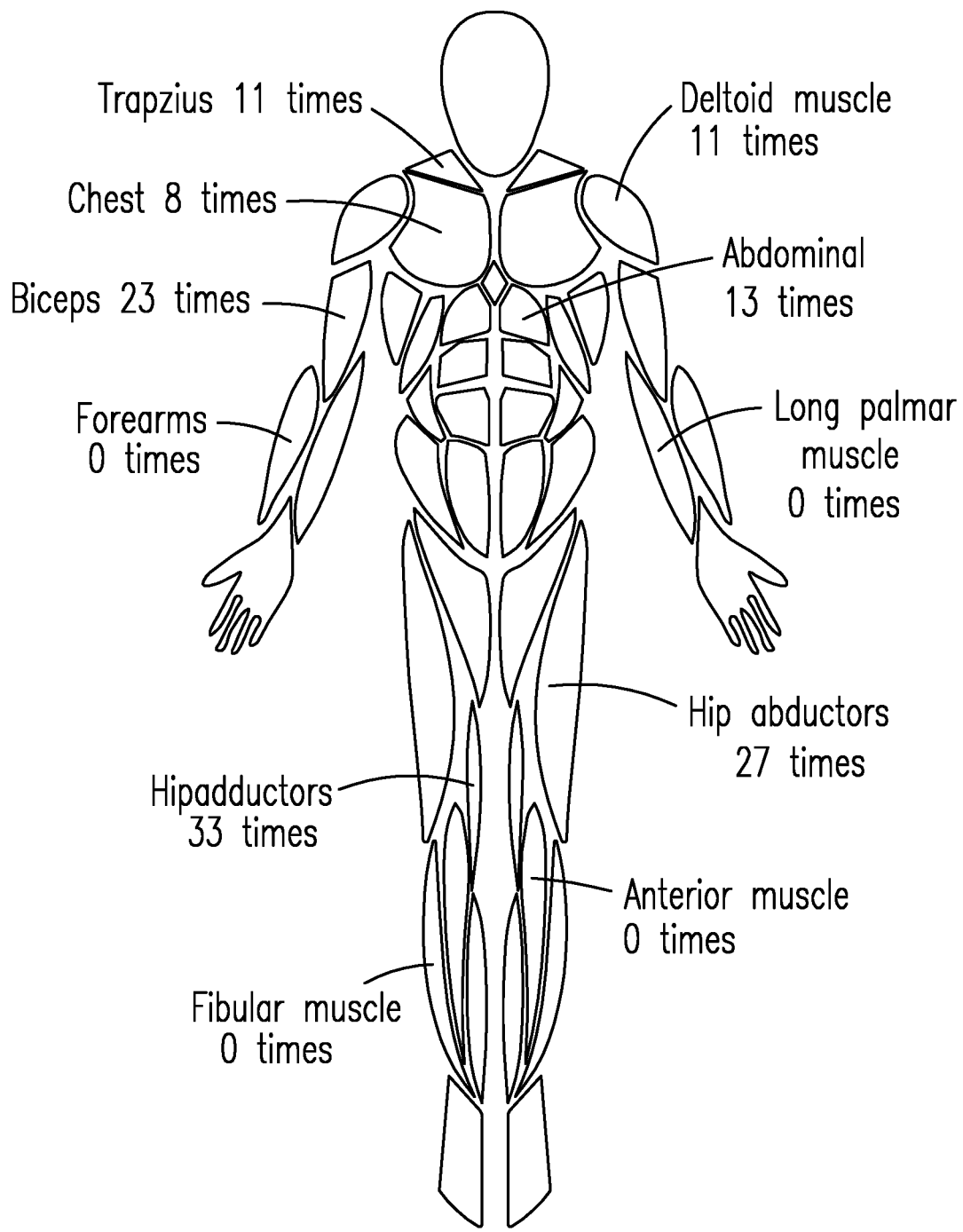
FIG. 3B is a schematic illustration of muscle recovery rates in accordance with a preferred embodiment of the present invention.
Figure 3C:
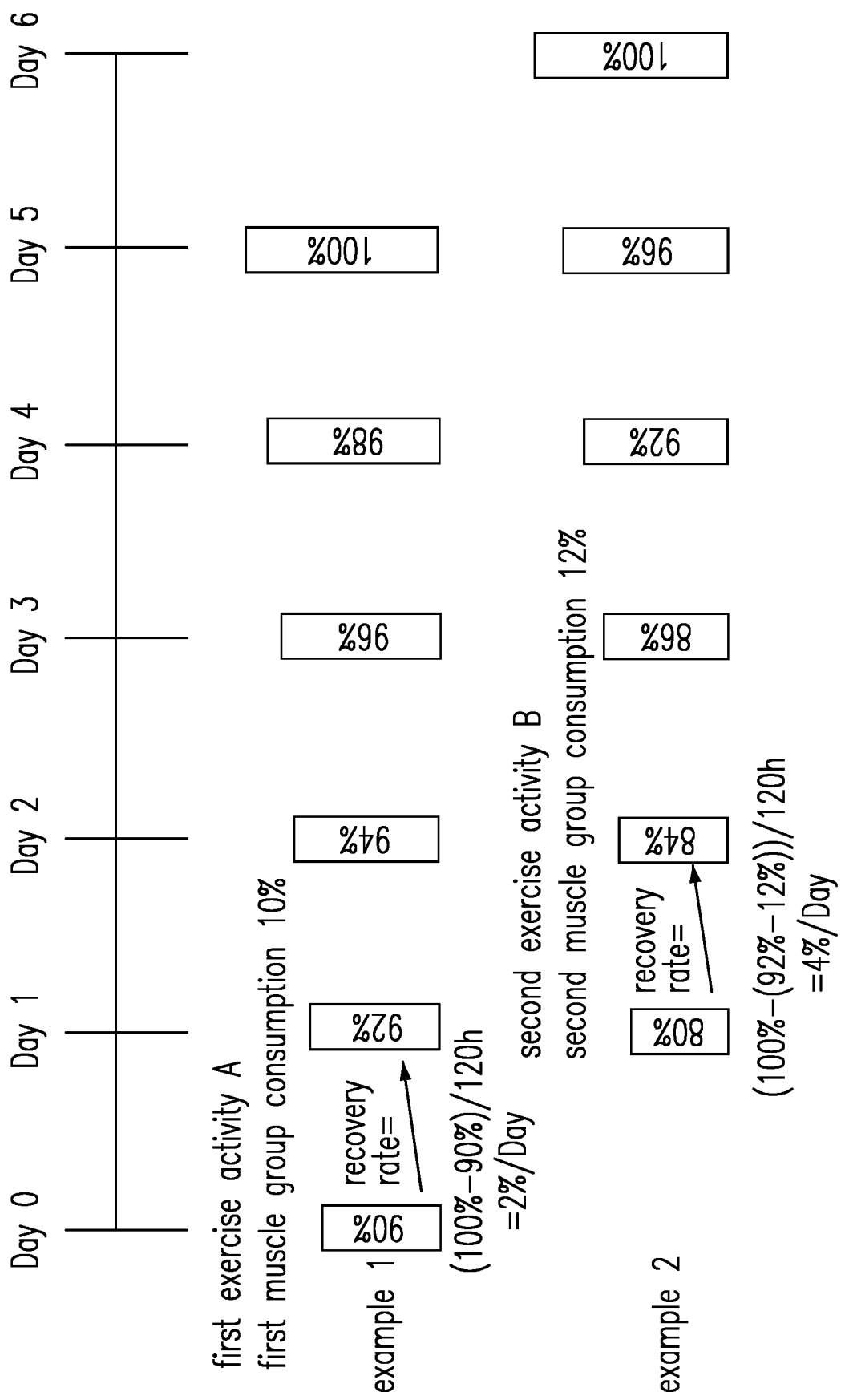
FIG. 3C is a schematic diagram of recovery rate calculation in accordance with preferred embodiment of the present invention.

Please return to FIG. 1B. In step S101, the system 10 can then be based on the degree of tiredness or fatigue of the muscle group after exercise or the degree of muscle recovery or recovery rate, as shown in FIGS. 3A and 3B. FIGS. 3A and 3B are schematic illustrations of muscle recovery rates in accordance with a preferred embodiment of the present invention showing the recovery rates of various muscle sites. The number of muscles or muscle groups that have not been exercised in FIG. 3A-3B is represented by 0 times. The number in FIG. 3C represents the recovery rate of muscles or muscle groups in percentage units. For example, 17 of the big muscles of the arm, representing a recovery rate of 17%. In a preferred embodiment of the invention, the rate of recovery is defined as the rate of muscle recovery after exercise. That is (remaining recovery rate−various sports muscle group consumption rate)=recovery rate. In a preferred embodiment of the invention, the recovery rate, regardless of the amount, is restored to 100% after consumption and then spending 120 hours. Therefore, it can be calculated the recovery rate according to how long the muscle or muscle group is resting after the exercise, and the degree of tiredness is defined as the difference between the ideal recovery rate of 100% and the current recovery rate, such as 75%, that is, 25%.

Please refer to FIG. 3C, which shows a schematic diagram of the recovery rate calculation of the preferred embodiment of the present invention. In FIG. 3C, after the fitness person performs a first exercise activity (Workout A) on a first muscle group on the 0th day, wherein the recovery rate of the muscle group is 100%, and after the exercise muscle group consumes 10%, the recovery rate remains (100%−10%)= 90%. Because the recovery rate is no matter how much, it takes 120 hours to recover to 100% after the consumption, so it takes 120 hours to recover from 90% to 100%, that is, rest for one day equals to 24 hours later, after calculation (24/120)×10%=2%, the recovery rate of the first muscle group increased by 2% after a day of rest, and the cumulative recovery rate is (90%+2%)=92%. Then, if the fitness is not continued, then after another day, that is, on the second day, the cumulative recovery rate is (92%+2%)=94%. If a continuous exercise is performed, for example, after doing the second exercise activity (Workout B) on the first day to continue to exercise the first muscle group, assuming that the exercise muscle group consumes 12%, the recovery rate remains (92%−12%)=80%. Because the recovery rate is no matter how much, it takes 120 hours to recover to 100% after consumption, so it takes 120 hours to recover from 80% to 100%, that is, after a day of rest=24 hours, it is restored after calculation (24/120)×20%=4%, so the recovery rate of the first muscle group increased by 4% after another day of rest, and the cumulative recovery rate is (80%+4%)=84%, that is, the cumulative recovery rate at daytime is 84% at the second day. Then, if the fitness is not continued, then after another day, that is, on the third day, the cumulative recovery rate is (84%+4%)=88%.

Figure 4A:
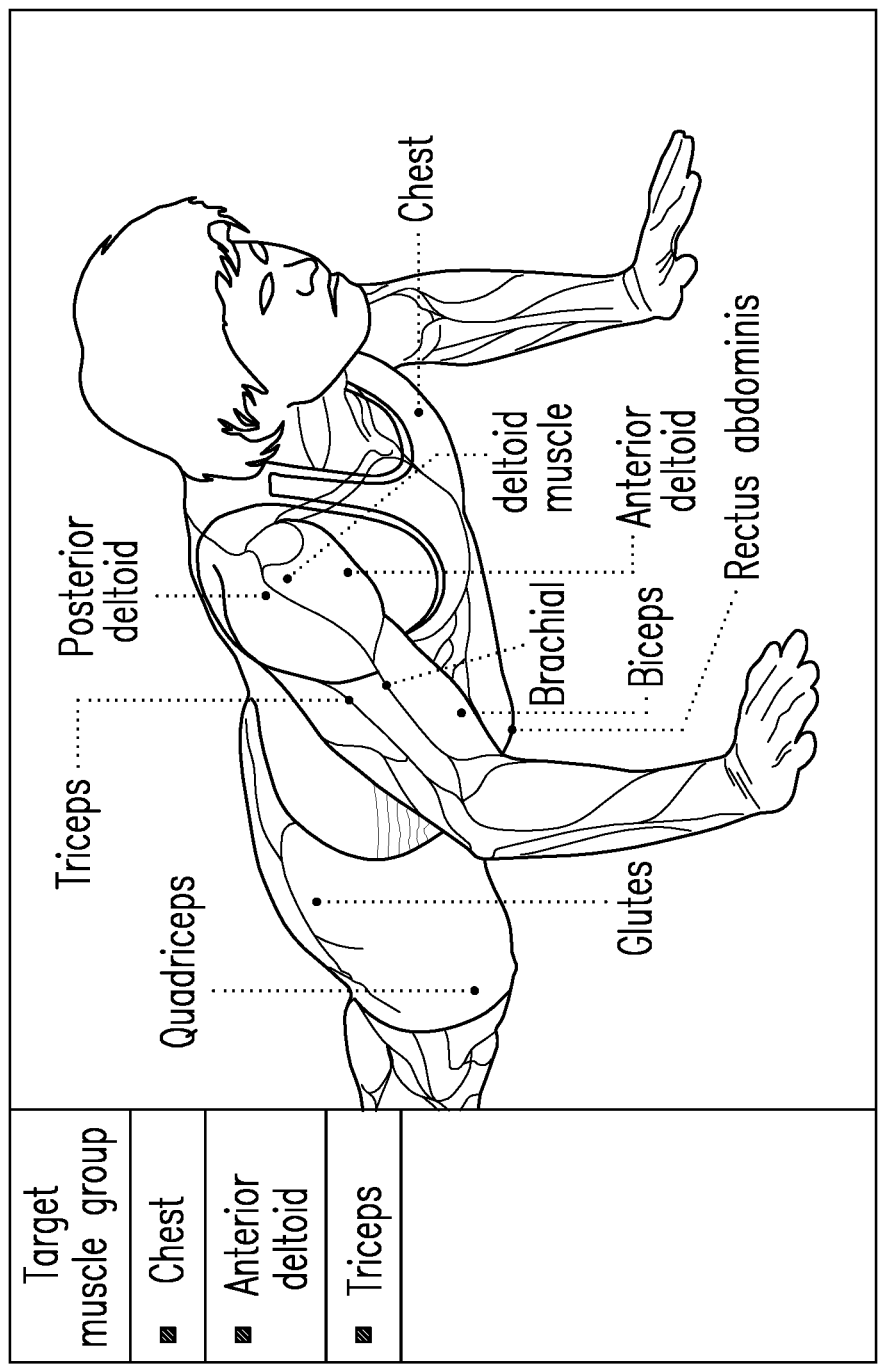
FIG. 4A is a schematic diagram of the push-up corresponding to the training muscle group part in a preferred embodiment of the present invention.
Figure 4B:
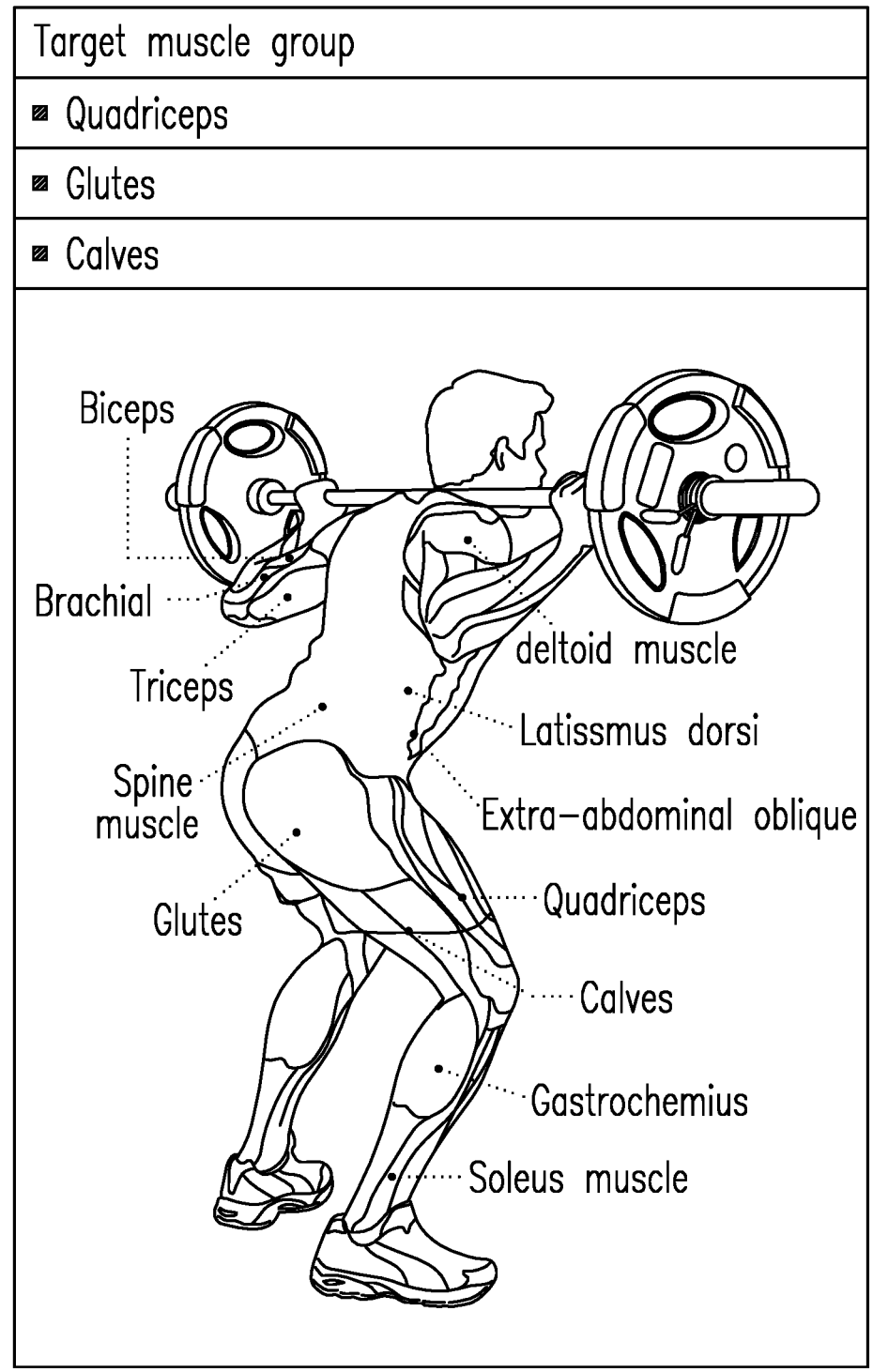
FIG. 4B is a schematic diagram of the barbell squatting corresponding to the training muscle group part in a preferred embodiment of the present invention.

Please return to step S102, the system 10 determines the suitable target muscle group according to the system fitness course database or the person personal fitness course database and the like, and makes recommendations. The system 10 can refer to the fitness course database, the personal fitness course database of the body builder, the muscle group or muscle and exercise training item, the single item or the curriculum correspondence table, and provide the bodybuilder with the corresponding exercise items list or the muscles or muscle groups to be trained or course recommendations. For example, the push-up corresponds to the training muscle group: chest muscle, deltoid anterior bundle, triceps, quadriceps, gluteal muscle and rectus abdominis, as shown in FIG. 4A, which is a schematic diagram of the push-up corresponding to the training muscle group part in a preferred embodiment of the present invention. For example, the barbell squat corresponds to the training muscle group parts: quadriceps, hind leg muscles, gluteal muscles, etc., as shown in FIG. 4B, which shows a schematic diagram of the barbell squatting corresponding to the training muscle group part in a preferred embodiment of the present invention.

In step S103, the system 10 may refer to the following factors to suggest a combination of courses, such as the recovery rate of muscles or muscle groups after exercise or training, as shown in FIGS. 3A and 3B: the exerciser or system 10 integrate a course combination suggestion according to the muscles or muscle groups must be trained; the predetermined muscle or muscle group's motion or training sequence; the number of sports or training items; and the order of muscle groups or muscle movements. The application's smart menu can be generated according to the selected trainable target muscle group, the target muscle group curriculum combination principle and rules, the relationship between the sports item list and the corresponding primary and secondary muscle groups, the method of selecting a course for the sports item selection, and a set of group number and exercise times of each item in the course. In step S103, the course is configured in accordance with the first three items, and then in the method of selecting a course for the sports item, in step S104, the course is configured according to the experience, level, and preference of the individual.

According to the above mentioned, grouping of the principles and methods of target muscle group are based on the classification of human muscle groups in Table 1, and the target muscle group curriculum combination principles and rules can select 3 main muscle groups+1 core muscle group according to the target muscle group. The selection method is based on the recovery rate, and the main muscle group is screened. Select the main muscle group with high recovery rate, and sort each main muscle group according to the high to low recovery rate. Select 5 main muscle groups with high recovery rate, and then select 3 from 5 main muscle groups. Only one of each group to which the muscle group belongs can be selected. Since the core grouping is a necessary grouping in the course, after the grouping is selected, the core grouping must be added. The selection method of core grouping is based on the selection of high recovery rate. As shown in the preferred embodiment of Table 2 below, the results of the high to low order are based on the recovery rate of the main muscle group.

TABLE 2

| Recovery rate | Main Muscle Group | Grouping | Chosen grouping | After selecting 3 in 5 based on recovery rate |
|---|---|---|---|---|
| 100% | Back | Upper Body | 1 | V |
| 100% | Chest | Upper Body | 1 | |
| 93% | Triceps | Upper extremity | 2 | V |
| 86% | Biceps | Upper extremity | 2 | |
| 86% | Quadriceps | Lower extremity | 3 | V |
| 45% | Shoulder | Shoulder | | |
| 45% | Hamstrings | Lower extremity | | |
| 42% | Glutes | Glutes | | |
| 42% | Shoulder | Shoulder | | |
| 38% | Abdominal | Abs | | V |
| 26% | Lower Back | Abs | | |

That is to say, the selection of the target muscle group is based on the recovery rate, and then the main muscle group is considered as a consideration.

Referring back to FIG. 1B, in step S104, a recommendation is made regarding the selection of a sports (or exercise) item, and the system 10 can add or delete sports or training items according to the following factors of the fitness person. For example, the fitness person's personal qualifications for fitness exercise, that is, a fitness exercise beginner, advanced person or the fitness exercise expert and other fitness exercise experience, that is, the fitness proficiency; the fitness person's personal preference for the fitness exercise program; and the fitness exercise history of the fitness person in the personal fitness training course database. The system 10 can increase or decrease the fitness exercise or training program for the proposed combination of courses.

In step S104, the application's smart menu can be generated into the sports item according to whether the user belongs to the preliminary, advanced, or expert level. For example, in Table 2, the priority is sorted by the recovery rate consideration, and then sorted according to the user's level or experience. If the user is a preliminary user, the selected three main muscle groups are sequentially assigned, and then two main muscle groups are randomly chosen from the three main muscle groups, and assigned to the corresponding sports items. If the user is an advanced user, the selected three main muscle groups are sequentially assigned, and then the three main muscle groups are individually and randomly supplemented with one auxiliary muscle group with a high recovery rate, and then two main muscle groups are randomly selected from the three main muscle group, and assigned to the corresponding sports items, plus one core muscle group item. If the user is an expert user, the selected three main muscle groups are sequentially assigned, and then the three main muscle groups are individually and randomly supplemented with one auxiliary muscle group with a high recovery rate, and then the three main muscle groups are randomly assigned to the corresponding sports item, plus one core muscle group item.

Table 3 below shows the results of the high and low order based on the recovery rate of the auxiliary muscle groups.

TABLE 3

| Recovery rate | Auxiliary muscle group | Grouping | Chosen grouping | Recovery rate consideration |
|---|---|---|---|---|
| 100% | Trapezius | Upper Body | — | V |
| 100% | Hip abductors | Glutes | | |
| 93% | Hip adductors | Glutes | | |
| 57% | Calves | Lower extremity | | |
| 50% | Forearms | Upper extremity | | |

In the relationship between the list of sports (exercise) items and the corresponding primary and secondary muscle groups, as shown in Table 4, there is a column for the difficulty level of expression, the menu action is randomly selected only by the difficulty level, and for the first-order users, are only randomly selected from the beginner's actions (rows). For, advanced users, the menu action can be randomly selected from the beginner's actions (rows) and/or advanced actions (rows). For professional users, the menu action can be randomly selected from the beginner's actions (rows) and/or advanced actions (rows) and/or professional actions (rows).

TABLE 4

| Exercise | Primary Muscle | Recovery Rate | Consumption Rate | Secondary Muscle | Recovery Rate | Consumption Rate | Equipment | Difficulty |
|---|---|---|---|---|---|---|---|---|
| Assisted Chin Up | Back | 52% | 48% | Biceps | 91% | 9% | Machine | Beginner |
| Assisted Neutral Grip Pull Up | Back | 52% | 48% | Biceps | 91% | 9% | Machine | Beginner |
| Assisted Pull Up | Back | 52% | 48% | Biceps | 91% | 9% | Machine | Beginner |
| Bar Muscle Up | Back | 73% | 27% | Abs | 95% | 5% | Body weight | Advanced |
| Barbell Row | Back | 52% | 48% | Biceps | 91% | 9% | Barbell | Beginner |
| Bent Over Barbell Row | Back | 52% | 48% | Biceps | 91% | 9% | Barbell | Beginner |
| Bent Over Row | Back | 52% | 48% | Biceps | 91% | 9% | Barbell | Beginner |
| Butterfly Pull Up | Back | 57% | 43% | Biceps | 92% | 8% | Body weight | Advanced |
| Cable Row | Back | 52% | 48% | Biceps | 91% | 9% | Cable | Beginner |
| Chin Up | Back | 57% | 43% | Biceps | 92% | 8% | Body weight | Intermediate |
| Dumbbell Row | Back | 52% | 48% | Biceps | 91% | 9% | Dumbbell | Beginner |

Table 5 shows a target muscle group of the menu for the beginner, the advanced use and the expert respectively.

TABLE 5

| | Target muscle group (Beginner) | Target muscle group (Advanced user) | Target muscle group (Expert) |
|---|---|---|---|
| 1 | Back | Back(Advanced) | Back(Expert) |
| 2 | Triceps | Triceps (Advanced) | Triceps (Expert) |
| 3 | Quadriceps | Quadriceps (Advanced) | Quadriceps (Expert) |
| 4 | Triceps | Trapezius (Advanced) | Trapezius (Expert) |
| 5 | Back | Triceps (Beginner) | Triceps (Advanced) |
| 6 | Abdominal | Back(Beginner) | Quadriceps (Advanced) |
| 7 | | Abdominal (All) | Back(Beginner) |
| 8 | | | Abdominal (All) |

In step S104, the method for selecting a sport item to be assigned to a course includes how to select a sport item, and the system 10 may select the sport item of the course according to the following steps: according to the user fitness experience value (beginner/advance/expert), and make random selection of sports according to the degree. Then according to the popularity; according to the user's personal preferences, for example: if the user likes some sport item, this sport item can be set as a big heart, then the output smart menu can be used as a choice of sports item basis. Further according to the environment preference, the user can set the environmental situation and use the switch mode to set. For example: Prefer for freehand sports item, prefer non-hands-free sports item, or without any preference. In the case of the free version, the setting of environmental preferences is divided into free-hand sports and non-hand-free sports; in the case of paid versions, the setting of environmental preferences can be combined with hand-free sports item and non-hand-free sports item of which the choice of equipment is alternatively added. For example, the dumbbell is the user's preferred equipment, and the butterfly machine is the user's preferred equipment. If the user does not set the environmental situation, the sport item is randomly selected. Finally, selecting the sport item is based on the user's history.

Each filtered item will be weighted, and the appropriate sports items in each stage will be selected according to the weights, as explained below. When the weight value is set according to the user's fitness experience value (beginner/advance/expert), the advanced items selected by the advanced user have preliminary and advanced, but the proportion of advanced sports item should be high, as shown in Table 6.

TABLE 6

| Item | Beginner's item | Advanced Item |
|---|---|---|
| Weight | 0.3 | 0.7 |

In the same way, the sports items selected for the expert users have three kinds of beginner advance and experts, but the proportion of the experts item should be high, followed by the advanced sports item, and finally the beginner sports item, as follows Table 7.

TABLE 7

| Item | Beginner's item | Advanced Item | Expert item |
|---|---|---|---|
| Weight | 0.1 | 0.3 | 0.6 |

According to the fitness experience value of the user, a suitable sports item list A (not shown) is selected.

When the weight value is set according to the popularity, and the so-called popularity refers to the database can be set in advance, the star rating is given for each sports item. At the same time, the ranking of the sports items that most users do is counted, and the star rating of the sports item is referenced. According to the level or its ordering, a list of sports items B (not shown) that match the user from the list of sports items A is selected. If there is no data in the database, the condition of the sports item is selected by the star rating.

When the system 10 sets the weight value according to the user's personal experience and preferences, the item can be provided for payment. The interface UI of the application allows the user to set the user's personal favorite sports item, and the favorite device includes, for example, a rope (Cable), Barbell, Dumbbell, or instruments (Machine). The user can also set the least favorite sports, the least favorite equipment, and so on, and the set items are stored in the database. The UI can be designed to use eight devices which are directly on/off, allowing the user to set which devices are preferred and store the settings in the database. The UI can also set favorite sports and store the settings in the database. If the user does not set personal preferences, such as a favorite sport, then the statistics of the user's personal sports and sports equipment are counted. After sorting, the sports items having the most repeated times are the most preferred item for the user. After statistics, the most commonly used equipment is the favorite equipment, the sports items that have not been done or the least number of times are the user's personal least favorite sports items, the least counted equipment, or equipment that is not used is the least favorite device. According to the generated sports item list B and then filtered according to the user's personal preference item, a sports item list C (not shown) is generated. If the user does not have a sports record, the user's personal favorite item cannot be listed. In this case, the database is set based on the UI interface. If there is no data set in the database, the random number is performed. The weights are as shown in Table 8.

TABLE 8

| Setting item | Favorite sports item | Least favorite sports item | Favorite equipment | Least favorite equipment |
|---|---|---|---|---|
| Weight | 0.4 | 0.1 | 0.4 | 0.1 |

Finally, the distribution of weights is generated based on the user's history. If the user has set personal preferences, the number of times which the user has done sports items is counted, and different weights are given according to the number of times. The level of number of times is divided into: 10 or less than 10 times (including 10 times) is level 0.1, 30 or less than 30 times (including 30 times) is level 0.2, 50 or less than 50 times (including 50 times) is level 0.2, 70 or less than 70 times (including 70 times) is level 0.2, and more than 70 times is level 0.3. The sports item list C is further filtered according to the user's historical record, and a sports item list D (not shown) is generated, and finally the sports item list D is the final sports item of the user menu.

Figure 5:
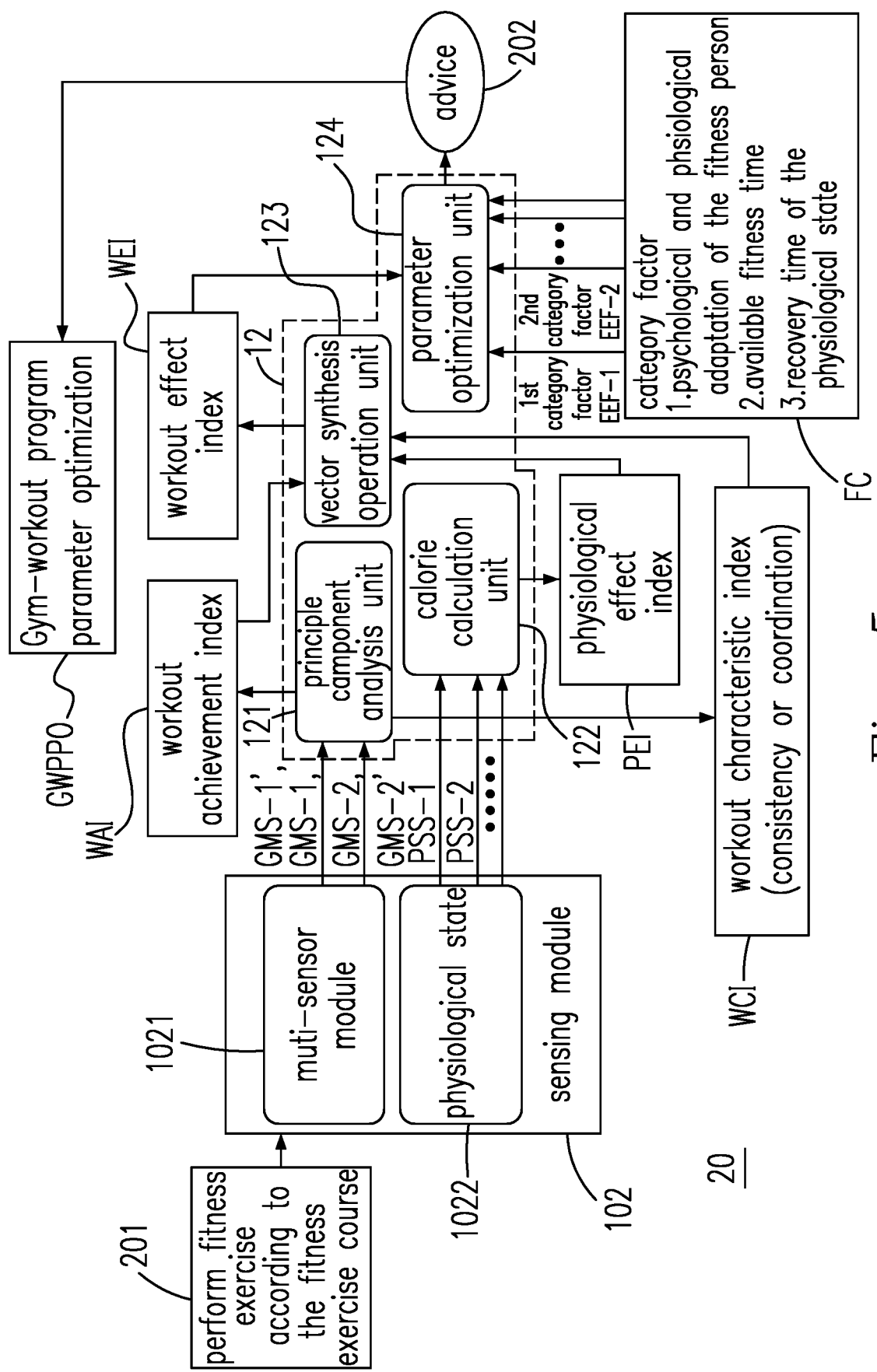
FIG. 5 is a schematic diagram of the revision device of the training course according to the preferred embodiment of the present invention.

Please refer to FIG. 1B again and FIG. 5, that is, the recommended exercise course after step S104 can be further evaluated by the sensing module 102 to evaluate the various factors mentioned above, and comprehensively judged to configure the number of groups for each item arranged in the course. Therefore, it is also possible to consider the muscle or muscle group tiredness or muscle strength recovery rate after fitness exercise or training, as shown in FIGS. 3A and 3B; the physical fitness experience and history of the fitness person personally, that is, a beginner level, advanced level athletes or fitness experts for fitness experience, and fitness training goals; and fitness training goals, such as endurance, muscle strength or muscle hypertrophy and other expected goals, etc. Then, a parameter configuration of the course, such as the total number of exercises, the number of exercise groups, the number of exercises per group, the exercise time of each group, the rest time between the two groups, and the total rest time and other parameters of the course are recommended.

Please return to FIG. 1B. In step S105, the system 10 proposes the times and number of groups of the sports items in the course as shown in FIG. 5. FIG. 5 is a schematic diagram of the revision device 20 of the training course according to the preferred embodiment of the present invention, which mainly includes the sensing module 102 and the processing unit 12, and the processing unit 12 suggests exercise and rest according to a plurality of algorithms and physiological states sensed by the sensing module 102. System 10 evaluates the fitness training program parameters and the recommended process as follows. First, the sensing module 102 in FIG. 1A includes a multi-sensor module 1021 and a physiological state sensing module 1022, as shown in FIG. 5. The multi-sensor module 1021 senses a plurality of limb motions of a fitness person and generates a plurality of limb motion signals, such as an acceleration signal GMS-1, an angular velocity signal GMS-2, an angle signal or a position signal (not shown). The multi-sensor module 1021 includes an accelerometer, a gyroscope and a geomagnetic meter to respectively generate the acceleration signal GMS-1 and the angular velocity signal GMS-2, and can correct the acceleration GMS-1 and the angular velocity signal GMS-2 by the sensed geomagnetic signal. The physiological state sensing module 1022 senses a physiological state of the fitness person and generates a physiological state signal, such as a heart rate signal PSS-1, a body temperature signal PSS-2, an oxygen consumption signal, and the like. The physiological state sensing module 1022 includes a heart rate meter, a body temperature sensor, and the like, so as to respectively sense the physiological state of the fitness person to generate the heart rate signal PSS-1 and the body temperature signal PSS-2, and can derive the relevant oxygen consumption by the heart rate signal PSS-1 and the body temperature signal PSS-2 by using the empirical formula.

In FIG. 5, the processing unit 12 includes a principle component analysis unit 121, a calorie calculation unit 122, a vector synthesis operation unit 123, and a parameter optimization unit 124. The principle component analysis unit 121 analyzes the principal component signals by using a plurality of limb motion signals GMS-1, GMS-2 by using a first algorithm (Principal Component Analysis—PCA), and then the principal component signals compares with the standard motion reference signal provided by the coach (or trainer) to correspond to a WCI (Workout Characteristic Index), such as a motion consistency quantized value, that is, compare with a coherence between a plurality of limb motion signals GMS-1, GMS-2 of the body builder and the standard motion reference signals GMS-1' and GMS-2' provided by the coach, so as to judge the training results or training effects. Alternatively, by comparing with the historical motion (exercise) signals of the exercisers themselves, judging the differences between the two signals, the progress of the fitness exercise of the fitness person can be understood. Alternatively, by comparing the above signals, the quantitative value of the coordination of the motion can be obtained. The PCA algorithm is used to analyze the acceleration signal GMS-1, the angular velocity signal GMS-2 and the information converted by the position-related signal, and then the motion characteristics are analyzed.

In FIG. 5, the WAI (Workout Achievement Index) is such as a muscle strength, a muscular endurance, and a change in muscle hypertrophy. Muscle strength refers to the force exerted by a muscle against a certain resistance force. Generally speaking, it refers to the maximum force that a muscle can produce when it contracts once. Muscle endurance is the amount of time or repetition times that a muscle can continue to exert when using a certain muscle strength. Muscle hypertrophy refers to the phenomenon that the muscle tissue of the body becomes thicker. As the name implies, the muscles look bigger and thicker. After increasing the contraction protein, the muscle fibers can be gradually enlarged, and the muscle cell can be increased through the progressive resistance motion. In general, muscle hypertrophy mainly presents two forms, that is, the increase of the contraction unit and the increase of the non-contraction unit.

The measurement of muscle strength is to measure the muscle strength of the muscle group or muscles of the bodybuilder after training, and compare the growth of muscle strength after the bodybuilder is engaged in the exercise fitness training course. As for the measurement method, the bodybuilder can operate 1 or 5 RM maximum load to evaluate. Alternatively, it is evaluated by the Velocity Based Training measured by motion measurement modules with accelerometers, gyroscopes, and electronic compasses. The measurement of muscular endurance is to measure the muscular endurance of the muscle groups or muscle of the bodybuilder after training, and compare the growth and development of the muscular endurance of the bodybuilder after training in the exercise fitness training course. The measurement of muscle hypertrophy is to measure the size of the muscle group or muscles of the bodybuilder after training, and compare the growth changes of the size of the muscle group or muscles related to the fitness training courses performed by the bodybuilder.

In FIG. 5, the calorie calculation unit 122 associates the physiological state signals PSS-1, PSS-2, etc. by an algorithm or a related formula to a physiological effect or a physiological phenomenon index PEI, such as a heart rate signal PSS-1. Through a second algorithm, that is, a calorie formula, a heart rate signal PSS-1 is corresponded to a physiological effect index PEI. The physiological effect index PEI is a calorie consumption, which is different for men and women respectively. Men calorie consumption= [(age×0.2017)+(body weight×0.09036)+(heart rate× 0.6309)−55.0969]×time/4.184; women calorie consumption=[(Age×0.074)−(Weight×0.05741)+(Heart Rate× 0.4472)×20.4022]×Time/4.184; Alternatively, the physiological state signal described above may be corresponding to an oxygen consumption amount via the associated oxygen consumption formula, thereby indicating the physiological effect index PEI.

In FIG. 5, the calorie calculation unit 123 converts the workout characteristic index WCI, the workout achievement index WAI (ie, exercise training achievement or exercise effect: muscle strength, muscular endurance, and muscle hypertrophy) and the physiological effect index PEI (ie, physiological phenomenon), into a fitness exercise performance index WEI (Workout Effect Index, i.e., a quantized consistence or coordination value, which is represented by the product or the vector sum of the muscle strength, the muscle endurance, the muscle hypertrophy and the calorie consumption) through a third algorithm (vector synthesis operation). The vector synthesis operation here is the calculation result of the square of the workout characteristic index WCI, the workout achievement index WAI and the physiological effect index PEI.

In FIG. 5, the parameter optimization unit 124 evaluates some factors associated with the workout effect index WEI, including the first category factor, the fitness outcome factor, ie, the workout characteristic index WCI, the workout achievement index WAI, and the physiological effect index PEI. The second category of factors is related to the fitness environment factor, that is, a time factor, a spatial factor, such as morning time is more spiritual for some people, and the fitness effect is better, or the comfort of the fitness place will also affect the fitness effect. The third category factor is related to a fitness action operation proficiency factor, and the like. The fourth category of factors is related to the psychological and physiological factors of the fitness person, namely the health factor and a psychological (likeness) factor. The parameter optimization unit 124 adjusts the content parameters of the training schedule by a fourth algorithm (parameter optimization method), that is, the training sequence of each exercise course, the entire time of the individual exercise courses, the allocated time of the individual operation periods thereof, or the operation of the training course, etc. (course content parameters include: number of exercises, exercise time, rest time, number of repetitions, . . . ). The Object Function or Cost Function in the parameter optimization method is the result of the motion recorded in the database, such as the WCI of the workout characteristic result mentioned above, the workout achievement index WAI, the physiological effect index PEI or the individual or integrated course parameters mapped by the WEI including the above three index, that is, the total number of exercises, the number of exercise groups, the number of exercises per group, the exercise time of each group, and the rest time between two groups and the total rest time arrangement, etc. It can be further combined with the constraints of optimizing the objective function, such as the fitness time available to the fitness person, the allowable physiological state, such as heart rate, the recovery rate of the muscle or the muscle group, class factors such as the psychological state of joy and the degree of subjective willingness to obtain the best course parameters. Finally, the display device 202 displays a gym-workout program parameter optimization GWPPO for reference and execution by the fitness person.

Figure 6:
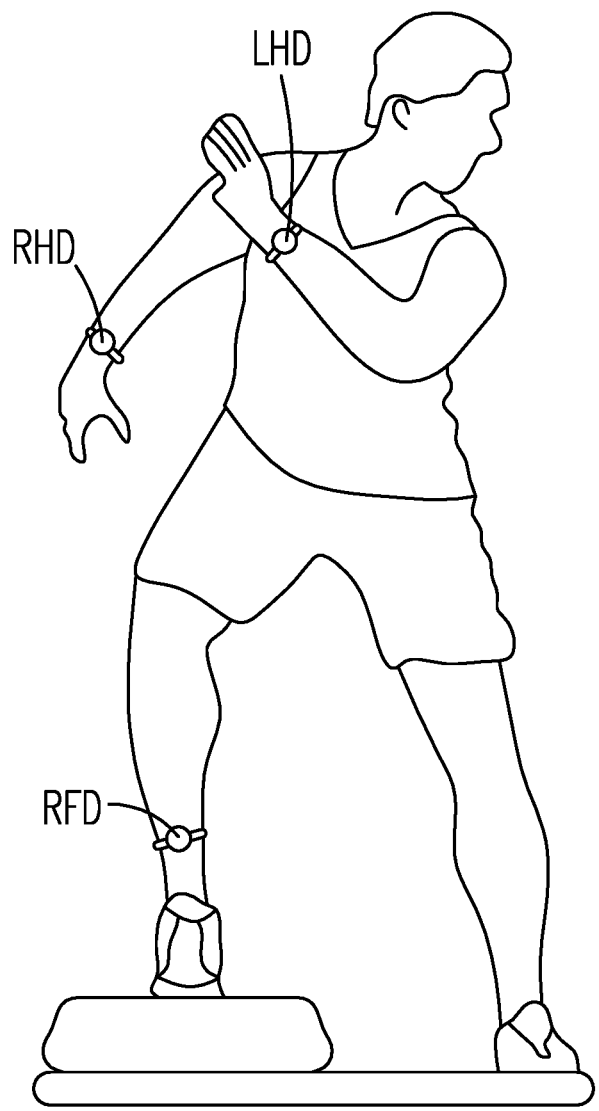
FIG. 6 is a schematic diagram of a sensing module disposed on a fitness person in accordance with a preferred embodiment of the present invention.

Please return to FIG. 1B. In step S106, the system 10 can generate the content of the personal fitness course according to the above suggestions. For the following description, please refer to FIGS. 1A, 1B, 5 and 6. FIG. 6 is a schematic diagram of a sensing module disposed on a fitness person in accordance with a preferred embodiment of the present invention. The exercise course recommended by the system 10 is adjusted by a revision device 20 comprising an exercise training course of the fitness training program parameter evaluation and suggestion process as shown in FIG. 5, the device 20 further includes an input device 201 for the content of the exercise course and a display device 202 for displaying the content of the exercise course, and the content includes at least one exercise course. In FIG. 5, the multi-sensor module 1021 includes a motion sensor such as an accelerometer, a gyroscope and a geomagnetic instrument. The multi-sensor module 1021 includes at least one left-hand motion sensing device LHD, a right-hand motion sensing device RHD and the right-foot motion sensing device RFD are worn on limbs of a fitness person, as shown in FIG. 6. When the fitness person refers to the fitness exercise curriculum for fitness exercise, the plurality of limb motions of the exerciser are measured to correspondingly generate a plurality of limb motion sensing signals GMS-1, GMS-2. The physiological state sensing module 1022 can include a heart rate meter or a thermometer for sensing the physiological state, ie, heart rate and body temperature, of the fitness person referring to the fitness exercise schedule to correspondingly generate a physiological state signal. The physiological state signal includes a heart rate signal PSS-1 and a body temperature signal PSS-2. The processing unit 12 is, for example, a data processing device having a motion characteristic corresponding function, which analyzes the plurality of limb motion signals GMS-1, such as GMS-1, using a principal component signal analysis algorithm (PCA). After the principle component signal of the GMS-1 and/or GMS-2 signals is obtained, it is compared with the standard motion reference signal provided by the coach or the fitness signal of the fitness person's own fitness record, so as to correspond to a workout characteristic index WCI, such as a sports consistency index or a motion coordination index. A physiological state corresponding function uses a reference heartbeat to calculate the calorie consumption algorithm, and is used the physiological state signal, that is, the heart rate signal PSS-1 to correspond to a first physiological phenomenon index PEI, that is, a calorie consumption. A fitness effect corresponding function converts a vector synthesis algorithm, combined with the workout characteristic index WCI and the workout achievement index WAI into the physiological phenomenon index PEI, and then the PEI is converted into a workout effect index WEI. A course parameter revision function adopts a concept of number optimization algorithm, by evaluating the fitness record of the fitness person or non-self, and then with a first category factor—fitness outcome factors, that is, the workout effect index WEI, a second category factor—fitness environment factors, such as time factor, a spatial factor, a distance factor, the third category factor—the fitness factor of the fitness person, that is, a preference factor for the exercise item for the fitness person, and a fourth category factor—the physiological factors of the fitness person, such as a vitality (health) factors, and a fitness action operation proficiency factor and other qualifications, to adjust the content parameters of the training schedule, including the training sequence of each sports(fitness) course, the entire time of individual sports courses or the configuration time of individual operating hours or training, the operation of the course, the number of groups, the number of motions of all or each group, all or the motion time of each group, all or the rest time between groups, the number of repetitions, and so on.

Figure 7:
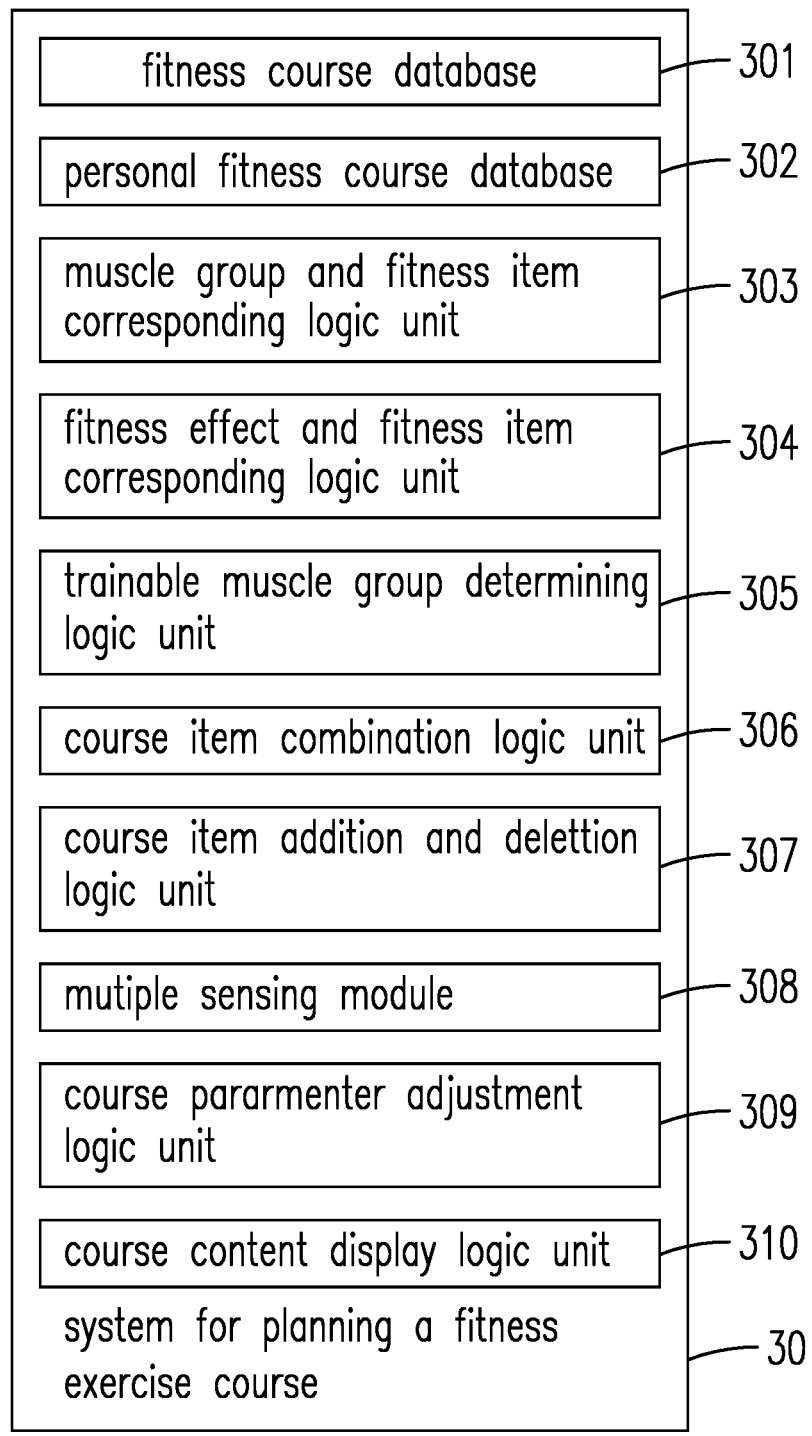
FIG. 7 is a schematic diagram of a system for planning a fitness exercise course according to another preferred embodiment of the present invention.

Please refer to FIG. 7, which is a schematic diagram of a system 30 for planning a fitness exercise course according to another preferred embodiment of the present invention. The system 30 for planning an exercise course includes a fitness course database 301, a personal fitness course database 302, a muscle group and fitness item corresponding logic unit 303, a fitness effect and fitness item corresponding logic unit 304, a trainable muscle group determining logic unit 305, a course item combination logic unit 306, a course item addition and deletion logic unit 307, a multiple sensing module 308, a course parameter adjustment logic unit 309, and a course content display logic unit 310. The fitness course database 301 stores at least one fitness course data and one fitness exercise data. The personal fitness course database 302 stores personal fitness course data of the fitness person and personal fitness exercise data of the fitness person. The muscle group and the fitness item corresponding logic unit 303 establish a muscle exercise corresponding data relationship suitable for training by a fitness item. The fitness effect and fitness item corresponding logic unit 304 provides a corresponding association or correspondence of a plurality of motion items or a plurality of motion items that allow the muscle group to achieve a training effect. The trainable muscle group determining logic unit 305 suggests a set of trainable muscle groups or a set of trainable muscles according to a physiological state of the fitness person. The course item combination logic unit 306 generates and configures a first part motion item of the plurality of motion item or a fitness item composed of a first part of the plurality of motion items according to the physiological state and the muscle group and fitness item corresponding logic unit 303. The course item addition and deletion logic unit 307 provides an item planning suggestion of the exercise course according to the fitness level datum of the fitness person, a willing (wish) data or a fitness experience datum. The multi-sensing module 308 correspondingly generates a plurality of limb motion sensing signals by sensing the plurality of limb motions of the fitness person to estimate the training effect. The course parameter adjustment logic unit 309 provides a parameter configuration suggestion of the exercise course according to the training effect, that is, the exercise (fitness) record. The parameter configuration includes a first plurality of exercise times, a plurality of exercise groups, the second plurality of exercise times included in each of the exercise training courses, an operation time of each of the exercise groups, a rest time between the two exercise groups, and a total operation time and a total rest time of the exercise training course. The course content display logic unit 310 presents a course content of a fitness curriculum by means of a presentation.

Please refer to FIGS. 5 and 7. The system 30 further includes a processing unit 12, wherein the multi-sensor module 1021 senses a plurality of limb motions (movements) of a coach to correspondingly generate a plurality of limb motion reference signals GMS-1', GMS-2', and will be temporarily stored in the system 30 or recorded signals GMS-1', GMS-2' in the fitness course database. Alternatively, by comparing the plurality of limb motion sensing signals GMS-1, GMS-2 with each other, generated by using the processing unit 12 and the exerciser, a coordination or consistency of the fitness person with respect to the fitness movement of the instructor is evaluated. The multi-sensor module 1021 includes an accelerometer sensing the acceleration of the fitness person, a gyroscope sensing the angular acceleration of the fitness person, and a heart rate meter sensing the physiological state of the fitness person.

Please also refer to FIGS. 5 and 7. The data of the plurality of sports items or the plurality of sports item is stored in a system course database 301. The training effect is about the endurance, the muscle strength and the growth of a muscle hypertrophy of the fitness person. The physiological state is a degree of tiredness (or fatigue) with respect to a muscle or a muscle group of the exerciser or a degree of recovery after exercise. The fitness level data (or profile) is configured to indicate fitness exercise proficiency with respect to a beginner, an advanced person, or an expert engaged in fitness. The willing datum (or material) is configured to represent a group of muscles about a subjective preference of the exerciser or the must-rained muscle group determined by the system. The fitness course data (material) is configured to represent a combination of at least one exercise item (program) or a plurality of exercise items (programs). The fitness experience datum (profile) is configured to represent an existing single person fitness course for the fitness person and stored in a single person fitness course library 302. The item adjustment suggestion (proposal) includes the deletion and layout of each training item (program). The exercise data is generated by a standard exercise signal GMS-1', GMS-2' sensed by the multi-sensor module 1021. The standard fitness signal GMS-1', GMS-2' is a sports feature signal of a fitness instructor. The presentation includes suggesting the posture or movement of the fitness person based on the type of the muscle group. The personal fitness course data (material) of the fitness person includes a person profile, and the personal data includes at least one of a name, a nickname, a gender, a date of birth, at least one favorite sports item, a daily exercise time and a physical health status.

Figure 8:
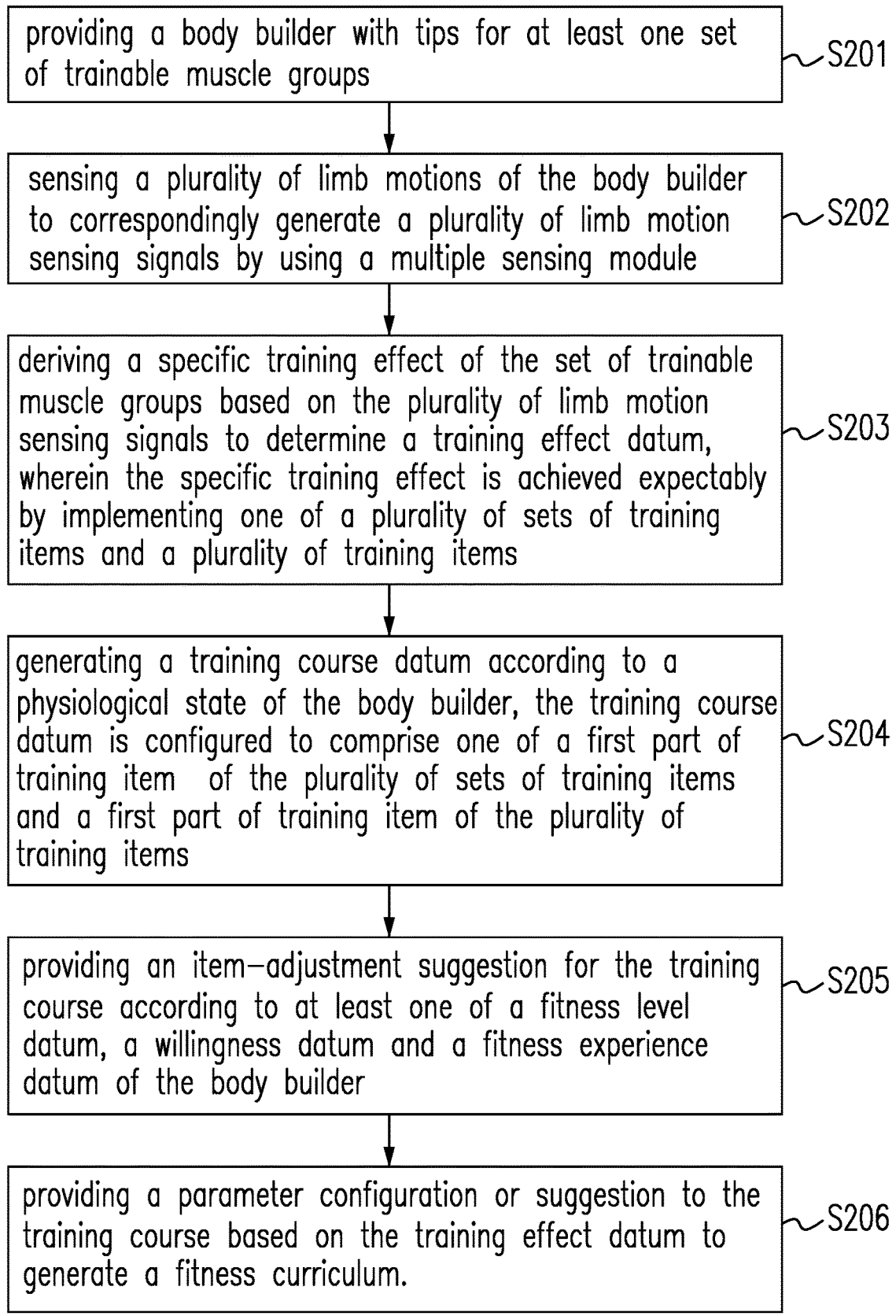
FIG. 8 is a schematic diagram of a method for planning a fitness exercise course according to a preferred embodiment of the present invention.

Please refer to FIG. 8, which is a schematic diagram of a method S20 for planning a fitness exercise course according to a preferred embodiment of the present invention. Step S201, providing a fitness person with a hit (or indication) for at least one set of trainable muscle groups. Step S202, sensing a plurality of limb motions of the fitness person by using a multiple sensing module to correspondingly generate a plurality of limb motion sensing signals. Step S203, estimating a specific training effect of the set of trainable muscle groups based on the plurality of limb motion sensing signals to determine a training effect datum, wherein the specific training effect is expected to be achieved and is performed by implementing a plurality of training item or a plurality of training items. Step S204, according to a physiological state of the fitness person, such as a muscle or a muscle group recovery rate or a physiological index such as tiredness, to generate a training course datum (material), the training course datum is configured to indicate the plurality of training items (courses) including a first part training items or a first part single training item. Step 205, providing an item adjustment suggestion of the training course according to the fitness level datum, the willing datum or the fitness experience datum of the fitness person. Step 206: providing a parameter configuration or suggestion of the training course according to the training effect datum, including WCI, WAI, PEI and WEI to generate a fitness curriculum.

Please also refer to FIGS. 5 and 8. The trainable muscle group is classified by anatomical muscle groups. The training effect is about the endurance, the muscle strength and the growth of a muscle hypertrophy of the fitness person. The method further includes the step of sensing a plurality of limb motions of a trainer by using the multi-sensor module 1021 to correspondingly generate a plurality of limb motion reference signals GMS-1', GMS-2'. By using the processing unit 12 to compare the plurality of limb motion reference signals GMS-1', GMS-2' and the plurality of limb motion sensing signals GMS-1, GMS-2, the coordination or consistency of the fitness person is evaluated.

Figure 9:
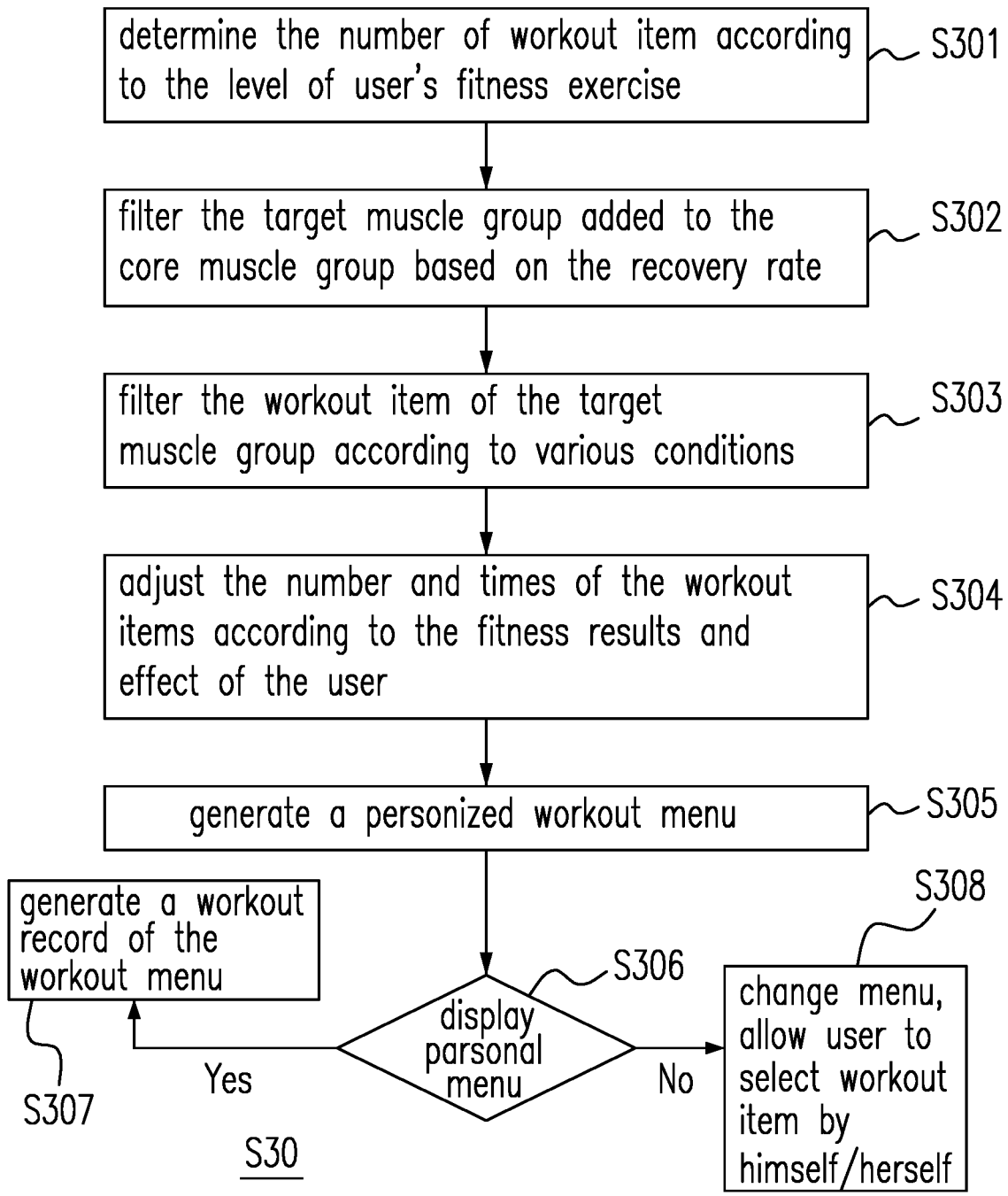
FIG. 9 is a schematic diagram of the flow of a system for planning a fitness course according to a preferred embodiment of the present invention

Please refer to FIG. 9, which is a schematic diagram of the flow S30 of a system 30 for planning a fitness course according to a preferred embodiment of the present invention. Step S301, the system 30 determines the number of workout items according to the level of the user's fitness exercise; in step S302, the target muscle group is filtered and added to the core muscle group based on the muscle state recovery rate of the user after fitness; step S303, according to various conditions, for example, refer to the user's intentions on the training results or training effects, the preference of the workout items or the difficulty of the workout items, the physiological adaptation to the workout items, the fitness time available for use, and the physiological state after the fitness, such as various conditions including the recovery state of the muscles are used to filter the workout items of the target muscle group; in step S303, adjust the number and times (frequency) of the workout items according to the fitness results and effects of the user; in step S305, generate a personalized workout menu; the user decides whether to execute the personalized menu, and if so, the process proceeds to step S307 to generate a workout record for performing the exercise according to the menu; if not, the process proceeds to step S308, the menu is changed to allow the user to select the workout item by himself/herself.

Embodiments

1. A method for planning a fitness exercise course, comprising the following steps: providing a body builder with tips for at least one set of trainable muscle groups; sensing a plurality of limb motions of the body builder to correspondingly generate a plurality of limb motion sensing signals by using a multiple sensing module; deriving a specific training effect of the set of trainable muscle groups based on the plurality of limb motion sensing signals to determine a training effect datum, wherein the specific training effect is to be achieved by implementing one of a plurality of sets of training items and a plurality of training items; generating a training course datum according to a physiological state of the body builder, wherein the training course datum is configured to comprise one of a first part of training items of the plurality of sets of training items and a first part of training items of the plurality of training items; providing an item-adjustment suggestion for the training course according to at least one of a fitness level datum, a willingness datum and a fitness experience datum of the body builder; and providing a parameter configuration or suggestion on the training course based on the training effect datum to generate a fitness curriculum.

2. The method in Embodiment 1, further comprising steps of: calculating one of a recovery rate and a degree of tiredness of the set of trainable muscle groups of the body builder; and ranking the set of trainable muscle groups according to one of the recovery rate and the degree of tiredness.

3. The method of any one of Embodiments 1-2, wherein the set of trainable muscle groups is categorized by anatomical muscle groups.

4. The method of any one of Embodiments 1-3, wherein the training effect is at least one of an endurance, a muscle strength and a growth of a muscle of the body builder.

5. The method of any one of Embodiments 1-4, further comprising steps of: sensing a plurality of limb motions of a trainer to correspondingly generate a plurality of limb motion reference signals by using the multiple sensing module; and comparing the plurality of limb motion reference signals and the plurality of limb motion sensing signals to evaluate at least one of a coordination and a consistency of the body builder by using a processing unit.

6. The method of any one of Embodiments 1-5, wherein the plurality of sets of training items and the plurality of training items are stored in a system course database; and the physiological state is associated with at least one of a degree of tiredness and a degree of recovery of a muscle or a muscle group of the body builder after an exercise.

7. The method of any one of Embodiments 1-6, wherein the fitness level datum is configured to indicate that the body builder is one of a fitness beginner, an advanced fitness person, and a fitness expert; the willingness datum is configured to represent at least one of a subjective preference of the body builder and a must-train muscle group determined by the method; and the fitness experience datum is configured to represent an existing individual fitness course for the body builder, and is stored in a fitness course database.

8. The method of any one of Embodiments 1-7, wherein the item-adjustment suggestion for the training course includes an addition, a deletion and a layout of each training item; and the parameter configuration is to allocate a number of total times of motion to a plurality of motion segments for the exercise item in the training course, assign a number of motion times to each of the motion segments, and an exercise time of a specific one of the motion segments, a rest time between two consecutive motion segments, and a total rest time.

9. A system for planning a fitness exercise course, comprising: a fitness course database storing at least one of a fitness course datum and a fitness exercise datum; a personal fitness course database storing a personal fitness course datum and a personal fitness exercise datum of a body builder; a muscle-group versus fitness-exercise-item logic unit establishing a corresponding data relationship of a muscle training in which a muscle group corresponds to a fitness exercise item; a fitness-effect versus fitness-exercise-item logic unit providing at least one of a plurality of exercise groups and a plurality of exercise items which allow the muscle group to achieve a training effect; a trainable-muscle-group-determining logic unit suggesting at least one of a set of trainable muscle groups and a group of trainable muscles according to a physiological state of the body builder; a-course-item-combination logic unit generating an exercise course configured to represent at least one of a first part of the plurality of exercise groups and a first part of the plurality of exercise items according to the physiological state by the muscle-group versus fitness-exercise-item logic unit; a course-item-adding-or-deleting logic unit providing an item-planning suggestion of the fitness exercise course according to at least one of a fitness level datum, a willingness datum and a fitness experience datum of the body builder; a multiple sensing module correspondingly generating a plurality of limb motion sensing signals by sensing a plurality of limb motions of the body builder to calculate the training effect; a course-parameter-adjustment logic unit providing a parameter-configuration suggestion to the fitness exercise course according to the training effect, wherein the parameter configuration suggestion includes a first plurality of exercise times, a plurality of exercise groups of the fitness exercise course, a second plurality of exercise times in each of the exercise groups, a training time of each of the exercise groups, a rest time between two consecutive exercise groups, a total training time and a total rest time configuration of the fitness exercise course; and a course-content-display logic unit presenting a course content of the fitness exercise course.

10. The system in Embodiment 9, further comprising a processing unit, wherein the multiple sensing module senses a plurality of limb motions of a coach to correspondingly generate a plurality of limb motion reference signals, and the processing unit compares the plurality of limb motion reference signals and the plurality of limb motion sensing signals to evaluate at least one of a coordination and consistency of the body builder; and the multiple sensing module includes an accelerometer meter sensing an acceleration of the body builder, a gyroscope sensing an angular acceleration of the body builder, and a heart rate meter sensing the physiological state of the body builder.

11. The system of any one of Embodiments 9-10, wherein the plurality of exercise groups and the plurality of exercise items are stored in a system course database; the training effect is related to at least one of an endurance, a muscle strength and a growth of a muscle of the body builder; and the physiological state is related to at least one of a degree of tiredness of a muscle, a muscle group, and a recovery of the body builder after an exercise.

12. The system of any one of Embodiments 9-11, wherein the fitness level datum is configured to indicate a fitness exercise skill level with respect to a beginner, an advanced person, or an expert engaged in fitness; and the willingness datum is configured to represent at least one of a subjective preference of the body builder and a must-train muscle group determined by the system.

13. The system of any one of Embodiments 9-12, wherein the fitness exercise course has data configured to represent a combination of at least one of an exercise fitness item and a plurality of exercise fitness items; and the fitness experience datum is configured to represent an existing individual fitness course for the body builder and is stored in a personal fitness course database.

14. The system of any one of Embodiments 9-13, wherein the item-planning suggestion of the fitness exercise course includes an item-adjustment suggestion including an addition, a deletion and a layout of each training item for the training course; the fitness exercise datum is generated by a standard fitness exercise signal sensed by the multiple sensing module; and the standard fitness exercise signal is a sport characteristic signal of a coach.

15. The system of any one of Embodiment 9-14, wherein the course-content-display logic unit suggests at least one of a posture and a motion of the body builder based on a type of the muscle group; and the personal fitness course datum of the body builder includes a personal datum including at least one of a name, a nickname, a gender, a date of birth, at least one of favorite sport items, a daily exercise time, and a physical health status.

16. A system for planning a fitness exercise course, comprising: a corresponding module establishing a corresponding relationship between a training target and each of a plurality of fitness exercise items, wherein the training target includes a specific muscle, a muscle group and a whole body muscle; a sensing module sensing a physiological state of a body builder; and a determining module, according to the corresponding relationship, in response to the physiological state, selecting one of the plurality of fitness exercise items and a combination of fitness exercise items to complete the training target.

17. The system in Embodiments 16, wherein the corresponding module further establishes the training target including a cardiopulmonary activity; the corresponding module further includes: a muscle-group versus fitness-exercise-item logical unit establishing a corresponding relationship of a muscle training between a muscle group and a fitness exercise item; and a fitness-effect versus fitness-exercise-item logical unit providing at least one of a plurality of exercise groups and a plurality of exercise items which allow the muscle group to achieve a training effect, wherein the training effect is related to at least one of an endurance, a muscle strength and a growth of a muscle of the body builder; and the sensing module senses the physiological state of the body builder to correspondingly generate a sensing signal to derive the training effect.

18. The system of any one of Embodiments 16-17, wherein the determining module includes: a trainable-muscle-group-determining logical unit suggesting at least one of a set of trainable muscle groups and a group of trainable muscles according to a physiological state of the body builder; and a course-item-combination logical unit generating an exercise course configured to represent at least one of a first part of the plurality of exercise groups and a first part of the plurality of exercise items according to the physiological state by the muscle-group versus fitness-exercise-item logical unit; a course-parameter-adjustment logical unit providing a parameter-configuration suggestion to the fitness exercise course according to the training effect, wherein the parameter-configuration suggestion includes a first plurality of exercise times, a plurality of exercise groups of the fitness exercise course, a second plurality of exercise times in each of the exercise groups, a training time of each of the exercise groups, a rest time between two consecutive exercise groups, a total training time and a total rest time configuration of the fitness exercise course; the system further includes a processing unit, wherein the sensing module senses a plurality of limb motions of a coach to correspondingly generate a plurality of limb motion reference signals, and the processing unit compares the plurality of limb motion reference signals and a plurality of limb motion sensing signals to evaluate at least one of a coordination and consistency of the bodybuilder; the sensing module includes an accelerometer sensing an acceleration of the plurality of limb motions of the body builder, a gyroscope sensing an angular acceleration of the body builder, and a heart rate meter sensing the physiological state of the body builder; and the system further includes a course-content-display logical unit presenting a course content of the fitness exercise course, and suggesting at least one of a posture and a motion of the body builder based on a type of the muscle group.

19. The system of any one of Embodiments 16-18, the system further comprising a fitness course database storing at least one of a fitness course datum and a fitness exercise datum; a personal fitness course database storing a personal fitness course datum and a personal fitness exercise datum of the body builder; and a course-item-adding-or-deleting logical unit providing an item-planning suggestion of the fitness exercise course according to at least one of a fitness level, a willingness and a fitness experience of the body builder.

20. The system of any one of Embodiments 16-19, wherein the plurality of exercise groups and the plurality of exercise items are stored in a system course database; the physiological state is related to at least one of a degree of tiredness of a muscle, a muscle group, and a recovery of the body builder after an exercise; the fitness level indicates that the body builder is one of a fitness beginner, an advanced fitness person, and a fitness expert; the willingness represents at least one of a subjective preference of the body builder and a must-train muscle group determined by the system; the fitness exercise course has a combination of at least one of an exercise fitness item and a plurality of exercise fitness items; the fitness experience represents an existing individual fitness course for the body builder, and is stored in the fitness course database; the item-planning suggestion of the fitness exercise course includes an item-adjustment suggestion including an addition, a deletion and a layout of each training item for the training course; the fitness exercise datum is generated by a standard fitness exercise signal sensed by the sensing module; the standard fitness exercise signal is a sport characteristic signal of a coach; the course-content-display logical unit suggests at least one of a posture and a motion of the body builder based on a type of the muscle group; and the personal fitness course datum of the body builder includes a personal datum including at least one of a name, a nickname, a gender, a date of birth, at least one of favorite sport items, a daily exercise time, and a physical health status.

While the invention has been described in terms of what is presently considered to be the most practical and preferred embodiments, it is to be understood that the invention need not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A system for planning a fitness exercise course, comprising:
   a multi-sensor module to sense a plurality of limb motions of a body builder exercising the fitness exercise course and generate a plurality of limb motion sensing signals;
   a physiological state sensing module to sense a physiological state of the body builder to generate a physiological state signal;
   a fitness course database storing at least one of a fitness course datum of the body builder and a fitness exercise datum related to the plurality of limb motions and the physiological state of the body builder;
   a personal fitness course database storing a personal fitness course datum and a personal fitness exercise datum for the body builder; and
   a processing unit processing the plurality of limb motion sensing signals and the physiological state signal, and configured to perform:
   establishing a corresponding data relationship between a muscle group and a fitness exercise item for a muscle training;
   providing at least one of a plurality of exercise groups and a plurality of exercise items including the fitness exercise item for the body builder to exercise a resistance motion training to achieve a training effect for the muscle group;
   suggesting at least one of a set of trainable muscle groups and a group of trainable muscles according to the physiological state of the body builder;
   generating the fitness exercise course to be stored in the fitness course data base, and is configured to represent a combination of at least one of a first part of the plurality of exercise groups and a first part of the plurality of exercise items according to the physiological state and the corresponding data relationship;
   providing an item-planning suggestion of the fitness exercise course according to at least one of a fitness level datum, a willingness datum and a fitness experience datum related to at least one of the plurality of limb motion sensing signals and the physiological state signal;
   providing a parameter-configuration suggestion to the fitness exercise course according to the training effect, wherein the parameter configuration suggestion includes a first plurality of exercise times, the plurality of exercise groups of the fitness exercise course, a second plurality of exercise times in each of the plurality of exercise groups, a training time of each of the plurality of exercise groups, a rest time between two consecutive exercise groups of the plurality of exercise groups, a total training time and a total rest time configuration of the fitness exercise course; and
   presenting a course content of the fitness exercise course.

2. The system as claimed in claim 1, wherein:
   the multi-sensor module senses a plurality of reference limb motions of a coach to correspondingly generate a plurality of limb motion reference signals, and the processing unit compares the plurality of limb motion reference signals and the plurality of limb motion sensing signals to evaluate at least one of a coordination and a consistency of the body builder related to the coach; and
   the multi-sensor module includes an accelerometer sensing an acceleration of the body builder, a gyroscope sensing an angular velocity of the body builder, and a heart rate meter sensing the physiological state of the body builder.

3. The system as claimed in claim 1, wherein:
   the plurality of exercise groups and the plurality of exercise items are stored in a system course database;
   the fitness exercise item trains a muscle by associating an anatomically trainable muscle group with the fitness exercise course;
   the training effect is related to at least one of an endurance, a muscle strength and a growth of the muscle of the body builder; and
   the physiological state is related to at least one of a degree of tiredness of the muscle, the muscle group, and a degree of recovery of the body builder after an exercise, wherein the degree of tiredness is defined as the difference between an ideal recovery rate and a current recovery rate of the body builder after the exercise, wherein the current recovery rate equals to a ratio of a rest time to a fully recovered time of the body builder times a percentage.

4. The system as claimed in claim 1, wherein:

the fitness level datum is configured to indicate a fitness exercise skill level with respect to a beginner, an advanced person, or an expert engaged in fitness; and the willingness datum is configured to represent at least one of a subjective preference of the body builder and a must-train muscle group determined by the system.

5. The system as claimed in claim 1, wherein:

the fitness exercise course has data configured to represent at least one exercise fitness item; and the fitness experience datum is configured to represent an existing individual fitness course for the body builder and is stored in the personal fitness course database.

6. The system as claimed in claim 1, wherein:

the item-planning suggestion of the fitness exercise course includes an item-adjustment suggestion including an addition, a deletion and a layout of each training item for the fitness exercise course;

the fitness exercise datum includes a standard fitness exercise signal sensed by the multi-sensor module; and the standard fitness exercise signal is a sport characteristic signal of a coach.

7. The system as claimed in claim 1, wherein:

the processing unit further performs suggesting at least one of a posture and a motion of the body builder based on a type of the muscle group; and the personal fitness course datum of the body builder includes a personal datum including at least one of a name, a nickname, a gender, a date of birth, at least one of favorite sport items, a daily exercise time, and a physical health status.

* * * * *